US007022896B1

(12) United States Patent
Weeks et al.

(10) Patent No.: US 7,022,896 B1
(45) Date of Patent: Apr. 4, 2006

(54) METHODS AND MATERIALS FOR MAKING AND USING TRANSGENIC DICAMBA-DEGRADING ORGANISMS

(75) Inventors: Donald P. Weeks, Lincoln, NE (US); Xiao-Zhuo Wang, Chapel Hill, NC (US); Patricia L. Herman, Waverly, NE (US)

(73) Assignee: Board of Regents of University of Nebraska, Lincoln, NE (US)

( * ) Notice: Subject to any disclaimer, the term of this patent is extended or adjusted under 35 U.S.C. 154(b) by 0 days.

(21) Appl. No.: 09/055,145

(22) Filed: Apr. 3, 1998

Related U.S. Application Data

(60) Provisional application No. 60/042,666, filed on Apr. 4, 1997, provisional application No. 60/042,941, filed on Apr. 4, 1997.

(51) Int. Cl.
*C12N 15/82* (2006.01)
*C12N 15/31* (2006.01)
*C12N 15/52* (2006.01)
*A01H 5/00* (2006.01)

(52) U.S. Cl. ............... 800/300; 435/252.3; 435/320.1; 435/419; 536/23.2; 536/23.7; 800/278

(58) Field of Classification Search ............. 435/320.1, 435/419, 418, 468; 536/23.2, 23.7, 24.1; 800/288, 300; 47/58.1
See application file for complete search history.

(56) References Cited

U.S. PATENT DOCUMENTS

| 4,816,403 A | 3/1989 | Roy .................. 435/253.3 |
| 5,362,865 A | 11/1994 | Austin .................. 536/24.1 |
| 5,445,962 A | 8/1995 | Atallah et al. ............ 435/252.1 |
| 5,545,818 A | 8/1996 | McBride et al. ............ 800/279 |
| 5,563,328 A | 10/1996 | Mitra et al. .................. 800/294 |
| 5,656,422 A | 8/1997 | Crawford et al. .............. 435/4 |
| 5,670,454 A | 9/1997 | Grossmann et al. ........ 504/244 |

FOREIGN PATENT DOCUMENTS

| CA | 2165036 | 6/1996 |
| WO | WO 97/41228 | 6/1997 |

OTHER PUBLICATIONS

Koziel, M. G. et al., "Optimizing expression of transgenes with an emphasis on post-transcriptional events." 1996, Plant Molecular Biology, vol. 32, pp. 393-405.*
Yuan, L. and Knauf, V. C. , "Modification of plant components." 1997, Plant biotechnology, vol. 8, pp. 227-233.*
Simisnszky et al., Expression of a soybean cytochrome P450 monoxygenase cDNA in yeast and tobacco enhaances the metabolism of phenylurea herbicides, Feb. 1999, Plant Biology, vol. 96, pp. 1750-1755.*
Donaldson et al 1991, Plant Physiology 96:669-674.*

Al-Khatib et al., 1992, *Weed Technology*, 6:57-61.
Baker, 1993, *Weed Technology*, 7:150-153.
Batie et al., *Chemistry and Biochemistry of Flavoenzymes*, vol. III, Chapter 18, pp. 543-556.
Batie et al., 1987, *J. Biol. Chem.*, 202(4):1510-1516.
Bernhardt et al., 1975, *Eur. J. Biochem.*, 57:241-256.
Cork et al., 1995, *Advances in Applied Microbiology*, 40: 289-320.
Cork et al., 1991, *Advances in Applied Microbiology*, 36:1-67.
Crop Protection Reference, 11th Edition, pp. 1803-1821 (1995).
Dehmel et al., 1995, *Arch Microbiol*, 163:35-41.
Fukumori et al., 1993, *J. Biological Chemistry*, 268(82): 24311-24317.
Harayama et al., 1992, *Ann. Rev. Microbiol*, 46:565-601.
Jasieniuk et al., 1995, *Weed Science*, 43:192-195.
Krueger et al., 1989, *J. Agric. Food Chem.*, 37:534-538.
Magnusson et al., 1987, *Weed-Science*, 35:846-852.
Markus et al., 1986, *J Biological Chem.*, 261(27):12883-12888.
Mason et al., 1992, *Ann. Rev. Microbiol.*, 46:277-305.
Meikle et al., 1995, Brighton Crop Protection Conference, *Weeds*, 5A-3:439-444.
Nakatsu et al., 1995, *Microbiology*, 141:485-495.
O'Keefe et al., 1991, *Biochemistry*, 30:447-455.
Peniuk et al., 1993, *Weed Research*, 33:431-440.

(Continued)

*Primary Examiner*—David H Kruse
(74) *Attorney, Agent, or Firm*—Sheridan Ross P.C.

(57) ABSTRACT

The invention provides isolated and at least partially-purified dicamba-degrading enzymes, isolated DNA molecules coding for dicamba-degrading enzymes, DNA constructs coding for dicamba-degrading enzymes, transgenic host cells comprising DNA coding for dicamba-degrading enzymes, and transgenic plants and plant parts comprising one or more cells comprising DNA coding for dicamba-degrading enzymes. Expression of the dicamba-degrading enzymes results in the production of dicamba-degrading organisms, including dicamba-tolerant plants. The invention further provides a method of controlling weeds in a field containing the transgenic dicamba-tolerant plants of the invention and a method of decontaminating a material containing dicamba comprising applying an effective amount of a transgenic microorganism or dicamba-degrading enzyme of the invention to the material. Finally, the invention provides a method of selecting transformed plants and plant cells based on dicamba tolerance and a method of selecting or screening transformed host cells, intact organisms and parts of organisms based on the fluorescence of 3,6-dichlorosalicylic acid produced as a result of dicamba degradation.

14 Claims, 1 Drawing Sheet

OTHER PUBLICATIONS

Romanov et al., 1994, *J. Bacteriology*, 176(11):3368-3374.
Rosche et al., 1995, *Biochimica et Biophysica Acta*, 1252: 177-179.
Sarpe et al., 1987, *Fragmenta herbologica Jugoslavica*, 16(1-2):299-305.
Schroeder et al., 1989, *Weed Technology*, 3:67-71.
Wang et al., 1997, *Applied and Environmental Microbiology*, 63(4):1623-1626.
Wang, "Characterization of Cellular and Enzymatic Degradation of Dicamba by *Pseudomonas maltophilia*, Strain DI-6," Thesis, University of Nebraska, (Thesis dated Aug. 1996).
Wicks et al., 1993, *Weed Science*, 41:225-231.
Yang et al., 1994, *Analytical Biochemistry*, 219:37-42.
Fogarty et al., *J. Inudstrial Microbiology*, 5:365-370 (1995).
Krueger et al., *J. Agric. Food Chem.*, 39:1000-1003 (1991).
Le et al., *J. of Bacteriology*, 175(23):7707-7710 (1993).
Wang et al., "A three component O-demethylase enzyme from *Pseudomonas maltophilia* catalyzes the first step in degradation of the herbicide, dicambe," vol. 95, 1995, p. 441, Abstract.
Weeks et al., "Characterization of a bacterial system capable of degrading dicambe and evluation of its potential in the development of herbicide-tolerant crops," *J. Cell. Biochem.*, Supp. No. 18, part I, 1994, p. 91, Abstract.

* cited by examiner

METHODS AND MATERIALS FOR MAKING AND USING TRANSGENIC DICAMBA-DEGRADING ORGANISMS

This application claims benefit of provisional application 60/042,666 and 60/042,941, both filed Apr. 4, 1997, the complete disclosures of which are incorporated herein by reference.

FIELD OF THE INVENTION

The present invention relates to transgenic organisms that are able to degrade the herbicide dicamba, including transgenic plants that have been made tolerant to dicamba. The invention also relates to dicamba-degrading enzymes and to DNA molecules and DNA constructs coding for dicamba-degrading enzymes. The invention further relates to a method of controlling weeds in fields of dicamba-tolerant transgenic plants and to a method of removing dicamba from materials contaminated with it (bioremediation). Finally, the invention relates to methods of selecting transformants based on dicamba tolerance or on detecting the fluorescence of 3,6-dichlorosalicylic acid which is generated as a result of dicamba degradation.

BACKGROUND

Herbicides are used routinely in agricultural production. Their effectiveness is often determined by their ability to kill weed growth in crop fields and the tolerance of the cash crop to the herbicide. If the cash crop is not tolerant to the herbicide, the herbicide will either diminish the productivity of the cash crop or kill it altogether. Conversely, if the herbicide is not strong enough, it may allow too much weed growth in the crop field which will, in turn, lessen the productivity of the cash crop. Therefore, it is desirable to produce economically important plants which are tolerant to herbicides. To protect the water and environmental quality of agricultural lands, it is also desirable to develop technologies to degrade herbicides in cases of accidental spills of the herbicide or in cases of unacceptably high levels of soil or water contamination.

Genes encoding enzymes which inactivate herbicides and other xenophobic compounds have previously been isolated from a variety of procaryotic and eucaryotic organisms. In some cases, these genes have been genetically engineered for successful expression in plants. Through this approach, plants have been developed which are tolerant to the herbicides 2,4-dichlorophenoxyacetic acid (Streber and Willmitzer (1989) *Bio/Technology* 7:811–816; 2,4-D), bromoxynil (Stalker et al. (1988) *Science* 242:419–423; tradname Buctril), glyphosate (Comai et al. (1985) *Nature* 317:741–744; tradname Round-Up) and phosphinothricin (De Block et al. (1987) *EMBO J.* 6:2513–2518; tradename Basta).

Dicamba (tradename Banvel) is used as a pre-emergent and post-emergent herbicide for the control of annual and perennial broadleaf weeds and several grassy weeds in corn, sorghum, small grains, pasture, hay, rangeland, sugarcane, asparagus, turf and grass seed crops. See *Crop Protection Reference*, pages 1803–1821 (Chemical & Pharmaceutical Press, Inc., New York, N.Y., 11th ed., 1995). Unfortunately, dicamba can injure many commercial crops (including beans, soybeans, cotton, peas, potatoes, sunflowers, tomatoes, tobacco, and fruit trees), ornamental plants and trees, and other broadleaf plants when it comes into contact with them. Id. Dicamba is chemically stable and can sometimes be persistent in the environment.

Dicamba is in the class of benzoic acid herbicides. It has been suggested that plants tolerant to benzoic acid herbicides, including dicamba, can be produced by incorporating a 1-aminocyclopropane-1-carboxylic acid (ACC) synthase antisense gene, an ACC oxidase antisense gene, an ACC deaminase gene, or combinations thereof, into the plants. See Canadian Patent Application 2,165,036 (published Jun. 16, 1996). However, no experimental data are presented in this application which demonstrate such tolerance.

Bacteria that metabolize dicamba are known. See U.S. Pat. No. 5,445,962; Krueger et al., *J. Agric. Food Chem.*, 37, 534–538 (1989); Cork and Krueger, *Adv. Appl. Microbiol.*, 38, 1–66 (1991); Cork and Khalil, *Adv. Appl. Microbiol.*, 40, 289–320 (1995). It has been suggested that the specific genes responsible for dicamba metabolism by these bacteria could be isolated and used to produce dicamba-resistant plants and other organisms. See id. and Yang et al., *Anal. Biochem.*, 219:37–42 (1994). However, prior to the present invention, no such genes had been identified or isolated.

SUMMARY OF THE INVENTION

The invention provides an isolated and at least partially purified dicamba-degrading O-demethylase, an isolated and at least partially purified dicamba-degrading oxygenase, an isolated and at least partially purified dicamba-degrading ferredoxin, and an isolated and at least partially purified dicamba-degrading reductase, all as defined and described below.

The invention also provides an isolated DNA molecule comprising a DNA sequence coding for a dicamba-degrading oxygenase and an isolated DNA molecule comprising a DNA sequence coding for a dicamba-degrading ferredoxin. The invention further provides a DNA construct comprising a DNA sequence coding for a dicamba-degrading oxygenase operatively linked to expression control sequences and a DNA construct comprising a DNA sequence coding for a dicamba-degrading ferredoxin operatively linked to expression control sequences.

The invention further provides a transgenic host cell comprising DNA coding for a dicamba-degrading oxygenase operatively linked to expression control sequences and a transgenic host cell comprising DNA coding for a dicamba-degrading ferredoxin operatively linked to expression control sequences. The transgenic host cell may comprise DNA coding for a dicamba-degrading oxygenase and a dicamba-degrading ferredoxin, both operatively linked to expression control sequences. The transgenic host cell may be a plant cell or a prokaryotic or eukaryotic microorganism.

In addition, the invention provides a transgenic plant or plant part comprising one or more cells comprising DNA coding for a dicamba-degrading oxygenase operatively linked to expression control sequences. The one or more cells of the plant or plant part may further comprise DNA coding for a dicamba-degrading ferredoxin operatively linked to expression control sequences. The transgenic plant or plant part is tolerant to dicamba or has its tolerance to dicamba increased as a result of the expression of the dicamba-degrading oxygenase or of the expression of the dicamba-degrading oxygenase and ferredoxin.

The invention also provides a method of controlling weeds in a field containing transgenic dicamba-tolerant plants according to the invention. The method comprises applying an amount of dicamba to the field which is effective to control the weeds.

The invention further provides methods of decontaminating a material containing dicamba. In one embodiment, the method comprises applying an effective amount of a transgenic dicamba-degrading microorganism of the invention to the material. In another embodiment, the method comprises applying an effective amount of a dicamba-degrading O-demethylase or of a combination of a dicamba-degrading oxygenase, a dicamba-degrading ferredoxin and a dicamba-degrading reductase to the material.

The invention also provides a method of selecting transformed plant cells and transformed plants using dicamba tolerance as the selection marker. In one embodiment, the method comprises transforming at least some of the plant cells in a population of plant cells with a DNA construct according to the invention and growing the resulting population of plant cells in a culture medium containing dicamba at a concentration selected so that transformed plant cells will grow and untransformed plant cells will not grow. In another embodiment, the method comprising applying dicamba to a population of plants suspected of comprising a DNA construct according to the invention which provides for dicamba degradation, the dicamba being applied in an amount selected so that transformed plants will grow, and the growth of untransformed plants will be inhibited.

Finally, the invention provides a method of selecting, or screening for, transformed host cells, intact organisms, and parts of organisms. The method comprises providing a population of host cells, intact organisms, or parts of organisms suspected of comprising a DNA construct according to the invention providing for dicamba degradation and ascertaining the presence or level of fluorescence due to 3,6-dichlorosalicylic acid. The 3,6-dichlorosalicyclic acid is generated in transformed host cells, intact organisms, or parts of organisms as a result of the degradation of dicamba, but will not be generated in untransformed host cells, intact orgnisms, or parts of organisms.

DETAILED DESCRIPTION OF THE PRESENTLY PREFERRED EMBODIMENTS OF THE INVENTION

Figure 1:
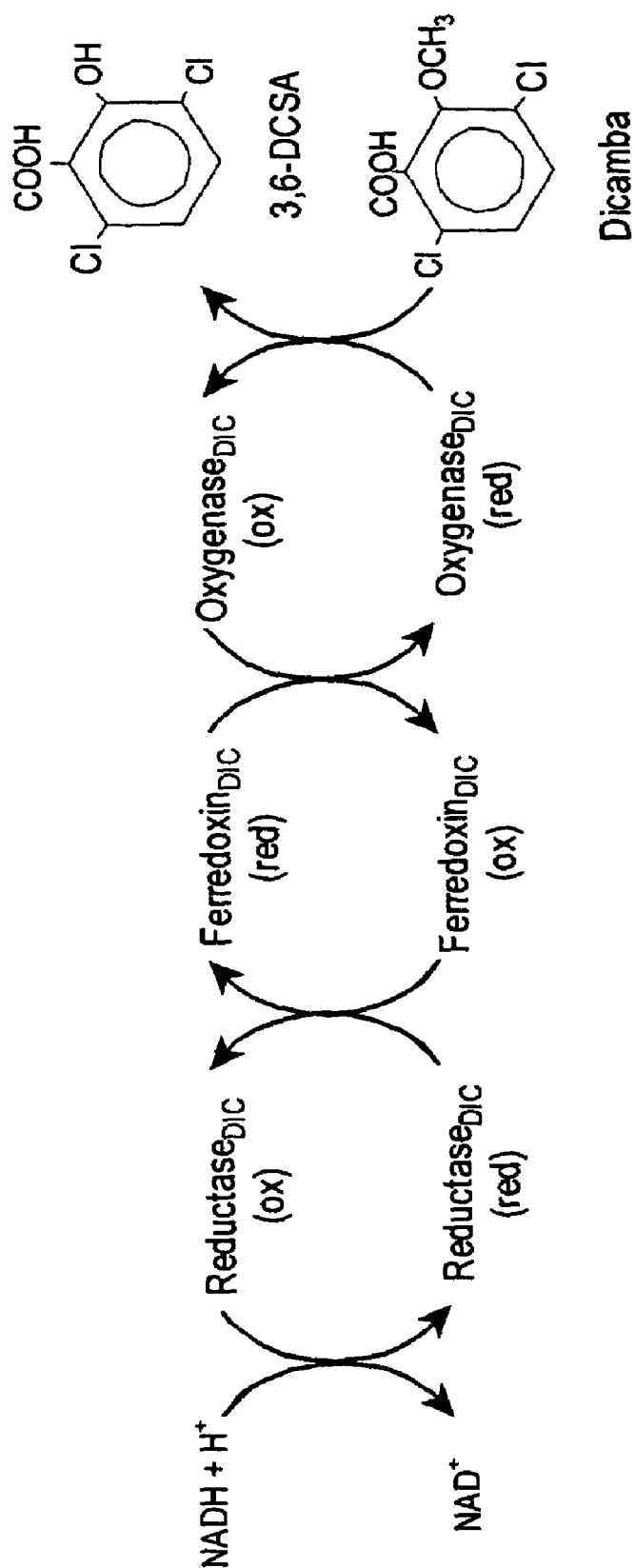
FIG. 1. A diagram of the proposed electron transport scheme for dicamba O-demethylase. Electrons from NADH are transferred sequentially from reductase$_{DIC}$ to ferredoxin$_{DIC}$ and then to oxygenase$_{DIC}$. The reaction of oxygen with the substrate dicamba to form 3,6-dichlorosalicylic acid is catalyzed by oxygenase$_{DIC}$. ox, oxidized; red, reduced.

Prior studies (Cork and Kreuger, *Advan. Appl. Microbiol.* 36:1–56 and Yang et al. (1994) *Anal. Biochem.* 219:37–42) have shown that the soil bacterium, *Pseudomonas maltophilia*, strain DI-6, is capable of destroying the herbicidal activity of dicamba through a single step reaction in which dicamba (3,6-dichloro-2-methoxybenzoic acid) is converted to 3,6-dichlorosalicylic acid (3,6-DCSA). 3,6-DCSA has no herbicidal activity and has not been shown to have any detrimental effects on plants. In addition, 3,6-DCSA is readily degraded by the normal bacterial flora present in soil.

The experiments described herein confirm the hypothesis of Yang et al. (see id.) that an O-demethylase is responsible for the conversion of dicamba to 3,6-DCSA by *P. maltophilia* strain DI-6 and establish that the O-demethylase is a three-component enzyme system consisting of a reductase, a ferredoxin, and an oxygenase. See Example 1 which describes in detail the isolation, purification and characterization of the *P. maltophilia* O-demethylase and its three components. The reaction scheme for the reaction catalyzed by the three components of dicamba O-demethylase is presented in FIG. 1. As illustrated in FIG. 1, electrons from NADH are shuttled through a short electron chain consisting of the reductase and ferredoxin to the terminal oxygenase which catalyzes the oxidation of dicamba to produce 3,6-DCSA.

In a first embodiment, the invention provides isolated and at least partially purified dicamba-degrading enzymes. "Isolated" is used herein to mean that the enzymes have at least been removed from the cells in which they are produced (i.e., they are contained in a cell lysate). "At least partially purified" is used herein to mean that they have been separated at least partially from the other components of the cell lysate. Preferably, the enzymes have been purified sufficiently so that the enzyme preparations are at least about 70% homogenous.

In particular, the invention provides an isolated and at least partially purified dicamba-degrading O-demethylase. "Dicamba-degrading O-demethylase" is defined herein to mean a combination of a dicamba-degrading oxygenase, a dicamba-degrading ferredoxin and a dicamba-degrading reductase, all as defined below.

The invention also provides an isolated and at least partially purified dicamba-degrading oxygenase. "Dicamba-degrading oxygenase" is defined herein to mean the oxygenase purified from *P. maltophilia* strain DI-6 and oxygenases which have an amino acid sequence which is at least about 65% homologous, preferably at least about 85% homologous, to that of the *P. maltophilia* oxygenase and which can participate in the degradation of dicamba. "Dicamba-degrading oxygenases" include mutant oxygenases having the amino acid sequence of the *P. maltophilia* oxygenase wherein one or more amino acids have been added to, deleted from, or substituted for, the amino acids of the *P. maltophilia* oxygenase sequence. Activity of dicamba-degrading oxygenases can be determined as described in Example 1.

The invention further provides an isolated and at least partially purified dicamba-degrading ferredoxin. "Dicamba-degrading ferredoxin" is defined herein to mean the ferredoxin purified from *P. maltophilia* strain DI-6 and ferredoxins which have an amino acid sequence which is at least about 65% homologous, preferably at least about 85% homologous, to that of the *P. maltophilia* ferredoxin and which can participate in the degradation of dicamba. "Dicamba-degrading ferredoxins" include mutant ferredoxins having the amino acid sequence of the *P. maltophilia* ferredoxin wherein one or more amino acids have been added to, deleted from, or substituted for, the amino acids of the *P. maltophilia* ferredoxin sequence. Activity of dicamba-degrading ferredoxins can be determined as described in Example 1.

Finally, the invention provides an isolated and at least partially purified dicamba-degrading reductase. "Dicamba-degrading reductase" is defined herein to mean the reductase purified from *P. maltophilia* strain DI-6 and reductases which have an amino acid sequence which is at least about 65% homologous, preferably at least about 85% homologous, to that of the *P. maltophilia* reductase and which can participate in the degradation of dicamba. "Dicamba-degrading reductases" include mutant reductases having the amino acid sequence of the *P. maltophilia* reductase wherein one or more amino acids have been added to, deleted from, or substituted for, the amino acids of the *P. maltophilia* reductase sequence. Activity of dicamba-degrading reductases can be determined as described in Example 1.

Methods of determining the degree of homology of amino acid sequences are well known in the art. For instance, the FASTA program of the Genetics Computing Group (GCG) software package (University of Wisconsin, Madison, Wis.) can be used to compare sequences in various protein databases such as the Swiss Protein Database.

The dicamba-degrading enzymes of the invention can be isolated and purified as described in Example 1 from *P. maltophilia* or other organisms. Suitable other organisms include bacteria other than *P. maltophilia* strain DI-6 that degrade dicamba. Several strains of such bacteria are known. See U.S. Pat. No. 5,445,962; Krueger et al., *J. Agric. Food Chem.*, 37, 534–538 (1989); Cork and Krueger, *Adv. Appl. Microbiol.*, 38, 1–66 (1991); Cork and Khalil, *Adv. Appl. Microbiol.*, 40, 289–320 (1995). Other dicamba-degrading bacterial strains can be isolated as were these strains by methods well known in the art.

Preferably, however, the dicamba-degrading enzymes of the invention are prepared using recombinant DNA techniques (see below). In particular, mutant enzymes having the amino acid sequence of the *P. maltophilia* enzyme wherein one or more amino acids have been added to, deleted from, or substituted for, the amino acids of the *P. maltophilia* sequence are prepared in this manner using, for example, oligonucleotide-directed mutagenesis, linker-scanning mutagenesis, mutagenesis using the polymerase chain reaction, and the like. See Ausubel et al. (eds.), *Current Protocols In Molecular Biology* (Wiley Interscience 1990) and McPherson (ed.), *Directed Mutagenesis: A Practical Approach* (IRL Press 1991).

In a second embodiment, the invention provides isolated DNA molecules coding for dicamba-degrading enzymes of the invention. "Isolated" is used herein to mean that the DNA molecule has been removed from its natural environment or is not a naturally-occurring DNA molecule. Methods of preparing these DNA molecules are well known in the art. See, e.g., Maniatis et al., *Molecular Cloning: A Laboratory Manual*, Cold Spring Harbor, N.Y. (1982), Sambrook et al., *Molecular Cloning: A Laboratory Manual*, Cold Spring Harbor, N.Y. (1989).

For instance, the DNA molecules of the invention may be isolated cDNA or genomic clones. The identification and isolation of clones coding for the dicamba-degrading oxygenase and ferredoxin of *P. maltophilia* strain DI-6 are described in Examples 2 and 3. Additional clones coding for dicamba-degrading enzymes, including clones coding for dicamba-degrading reductases, can be obtained in a similar manner. The isolated clones, or portions of them, can be used as probes to identify and isolate additional clones from organisms other than the ones from which the clones were originally isolated. Suitable organisms include bacteria that degrade dicamba. As noted above, in addition to *P. maltophilia* strain DI-6, several strains of bacteria are known that degrade dicamba. See U.S. Pat. No. 5,445,962; Krueger et al., *J. Agric. Food Chem.*, 37, 534–538 (1989); Cork and Krueger, *Adv. Appl. Microbiol.*, 38, 1–66 (1991); Cork and Khalil, *Adv. Appl. Microbiol.*, 40, 289–320 (1995).

The DNA molecules of the invention can also be chemically synthesized using the sequences of isolated clones. Such techniques are well known in the art. For instance, DNA sequences may be synthesized by phosphoamidite chemistry in an automated DNA synthesizer. Chemical synthesis has a number of advantages. In particular, chemical synthesis is desirable because codons preferred by the host in which the DNA sequence will be expressed may be used to optimize expression. Not all of the codons need to be altered to obtain improved expression, but preferably at least the codons rarely used in the host are changed to host-preferred codons. High levels of expression can be obtained by changing greater than about 50%, most preferably at least about 80%, of the codons to host-preferred codons. The codon preferences of many host cells are known. See, e.g., *Maximizing Gene Expression*, pages 225–85 (Reznikoff & Gold, eds., 1986), PCT WO 97/31115, PCT WO 97/11086, EP 646643, EP 553494, and U.S. Pat. Nos. 5,689,052, 5,567,862, 5,567,600, 5,552,299 and 5,017, 692. The codon preferences of other host cells can be deduced by methods known in the art. Also, using chemical synthesis, the sequence of the DNA molecule or its encoded protein can be readily changed to, e.g., optimize expression (e.g., eliminate mRNA secondary structures that interfere with transcription or translation), add unique restriction sites at convenient points, delete protease cleavage sites, etc.

In a third embodiment, the present invention provides DNA constructs comprising DNA coding for a dicamba-degrading enzyme operatively linked to expression control sequences. "DNA constructs" are defined herein to be constructed (non-naturally occurring) DNA molecules useful for introducing DNA into host cells, and the term includes chimeric genes, expression cassettes, and vectors.

As used herein "operatively linked" refers to the linking of DNA sequences (including the order of the sequences, the orientation of the sequences, and the relative spacing of the various sequences) in such a manner that the encoded proteins are expressed. Methods of operatively linking expression control sequences to coding sequences are well known in the art. See, e.g., Maniatis et al., *Molecular Cloning: A Laboratory Manual*, Cold Spring Harbor, N.Y. (1982), Sambrook et al., *Molecular Cloning: A Laboratory Manual*, Cold Spring Harbor, N.Y. (1989).

"Expression control sequences" are DNA sequences involved in any way in the control of transcription or translation in prokaryotes and eukaryotes. Suitable expression control sequences and methods of making and using them are well known in the art.

The expression control sequences must include a promoter. The promoter may be any DNA sequence which shows transcriptional activity in the chosen host cell or organism. The promoter may be inducible or constitutive. It may be naturally-occurring, may be composed of portions of various naturally-occuring promoters, or may be partially or totally synthetic. Guidance for the design of promoters is provided by studies of promoter structure, such as that of Harley and Reynolds, *Nucleic Acids Res.*, 15, 2343–61 (1987). Also, the location of the promoter relative to the transcription start may be optimized. See, e.g., Roberts, et al., *Proc. Natl. Acad. Sci. USA,* 76, 760–4 (1979). Many suitable promoters for use in prokaryotes and eukaryotes are well known in the art.

For instance, suitable constitutive promoters for use in plants include: the promoters from plant viruses, such as the 35S promoter from cauliflower mosaic virus (Odell et al., *Nature* 313:810–812 (1985), promoters of *Chlorella* virus methyltransferase genes (U.S. Pat. No. 5,563,328), and the full-length transcript promoter from figwort mosaic virus (U.S. Pat. No. 5,378,619); the promoters from such genes as rice actin (McElroy et al., *Plant Cell* 2:163–171 (1990)), ubiquitin (Christensen et al., *Plant Mol. Biol.* 12:619–632 (1989) and Christensen et al., *Plant Mol. Biol.* 18:675–689 (1992)), pEMU (Last et al., *Theor. Appl. Genet.* 81:581–588 (1991)), MAS (Velten et al., *EMBO J.* 3:2723–2730 (1984)), maize H3 histone (Lepetit et al., *Mol. Gen. Genet.* 231:

276–285 (1992) and Atanassova et al., *Plant Journal* 2(3): 291–300 (1992)), *Brassica napus* ALS3 (PCT application WO 97/41228); and promoters of various *Agrobacterium* genes (see U.S. Pat. Nos. 4,771,002, 5,102,796, 5,182,200, 5,428,147).

Suitable inducible promoters for use in plants include: the promoter from the ACE1 system which responds to copper (Mett et al. *PNAS* 90:4567–4571 (1993)); the promoter of the maize In2 gene which responds to benzenesulfonamide herbicide safeners (Hershey et al., *Mol. Gen. Genetics* 227:229–237 (1991) and Gatz et al., *Mol. Gen. Genetics* 243:32–38 (1994)), and the promoter of the Tet repressor from Tn10 (Gatz et al., *Mol. Gen. Genet.* 227:229–237 (1991). A particularly preferred inducible promoter for use in plants is one that responds to an inducing agent to which plants do not normally respond. An exemplary inducible promoter of this type is the inducible promoter from a steroid hormone gene, the transcriptional activity of which is induced by a glucocorticosteroid hormone. Schena et al., *Proc. Natl. Acad. Sci. USA* 88:10421 (1991). Other inducible promoters for use in plants are described in EP 332104, PCT WO 93/21334 and PCT WO 97/06269.

Suitable promoters for use in bacteria include the promoter of the *Bacillus stearothermophilus* maltogenic amylase gene, the *Bacillus licheniformis* alpha-amylase gene, the *Bacillus amyloliquefaciens* BAN amylase gene, the *Bacillus subtilis* alkaline protease gene, the *Bacillus pumilus* xylosidase gene, the phage lambda $P_R$ and $P_L$ promoters, and the *Escherichia coli* lac, trp and tac promoters. See PCT WO 96/23898 and PCT WO 97/42320.

Suitable promoters for use in yeast host cells include promoters from yeast glycolytic genes, promoters from alcohol dehydrogenase genes, the TPI1 promoter, and the ADH2-4c promoter. See PCT WO 96/23898.

Suitable promoters for use in filamentous fungi include the ADH3 promoter, the tpiA promoter, the promoters of the genes encoding *Aspergillus oryzae* TAKA amylase, *Rhizomucor miehei* aspartic proteinase, *Aspergillus niger* neutral alpha-amylase, *A. niger* acid stable alpha-amylase, *A. niger* or *Aspergillus awamori* glucoamylase, *R. miehei* lipase, *A. oryzae* alkaline protease, *A. oryzae* triose phosphate isomerase, and *Aspergillus nidulans* acetamidase. See PCT WO 96/23898.

Suitable promoters for use in mammalian cells are the SV40 promoter, metallothionein gene promoter, murine mammary tumor virus promoter, Rous sarcoma virus promoter, and adenovirus 2 major late promoter. See PCT WO 96/23898 and PCT WO 97/42320.

Suitable promoters for use in insect cells include the polyhedrin promoter, P10 promoter, the *Autographa californica* polyhedrosis virus basic protein promoter, the baculovirus immediate early gene 1 promoter and the baculovirus 39K delayed-early gene promoter. See PCT WO 96/23898.

Finally, promoters composed of portions of other promoters and partially or totally synthetic promoters can be used. See, e.g., Ni et al., *Plant J.*, 7:661–676 (1995)and PCT WO 95/14098 describing such promoters for use in plants.

The promoter may include, or be modified to include, one or more enhancer elements. Preferably, the promoter will include a plurality of enhancer elements. Promoters containing enhancer elements provide for higher levels of transcription as compared to promoters which do not include them. Suitable enhancer elements for use in plants include the 35S enhancer element from cauliflower mosaic virus (U.S. Pat. Nos. 5,106,739 and 5,164,316) and the enhancer element from figwort mosaic virus (Maiti et al., *Transgenic Res.*, 6, 143–156 (1997)). Other suitable enhancers for use in other cells are known. See PCT WO 96/23898 and *Enhancers And Eukaryotic Expression* (Cold Spring Harbor Press, Cold Spring Harbor, N.Y., 1983).

For efficient expression, the coding sequences are preferably also operatively linked to a 3' untranslated sequence. The 3' untranslated sequence contains transcription and/or translation termination sequences. The 3' untranslated regions can be obtained from the flanking regions of genes from bacterial, plant or other eukaryotic cells. For use in prokaryotes, the 3' untranslated region will include a transcription termination sequence. For use in plants and other eukaryotes, the 3' untranslated region will include a transcription termination sequence and a polyadenylation sequence. Suitable 3' untranslated sequences for use in plants include those of the cauliflower mosaic virus 35S gene, the phaseolin seed storage protein gene, the pea ribulose biphosphate carboxylase small subunit E9 gene, the soybean 7S storage protein genes, the octopine synthase gene, and the nopaline synthase gene.

In plants and other eukaryotes, a 5' untranslated sequence is also employed. The 5' untranslated sequence is the portion of an mRNA which extends from the 5' CAP site to the translation initiation codon. This region of the mRNA is necessary for translation initiation in eukaryotes and plays a role in the regulation of gene expression. Suitable 5' untranslated regions for use in plants include those of alfalfa mosaic virus, cucumber mosaic virus coat protein gene, and tobacco mosaic virus.

As noted above, the DNA construct may be a vector. The vector may contain one or more replication systems which allow it to replicate in host cells. Self-replicating vectors include plasmids, cosmids and viral vectors. Alternatively, the vector may be an integrating vector which allows the integration into the host cell's chromosome of the sequence coding for a dicamba-degrading enzyme of the invention. The vector desirably also has unique restriction sites for the insertion of DNA sequences. If a vector does not have unique restriction sites, it may be modified to introduce or eliminate restriction sites to make it more suitable for further manipulations.

The DNA constructs of the invention can be used to transform a variety of host cells (see below). A genetic marker must be used for selecting transformed host cells ("a selection marker"). Selection markers typically allow transformed cells to be recovered by negative selection (i.e., inhibiting growth of cells that do not contain the selection marker) or by screening for a product encoded by the selection marker.

The most commonly used selectable marker gene for plant transformation is the neomycin phosphotransferase II (nptII) gene, isolated from Tn5, which, when placed under the control of plant regulatory signals, confers resistance to kanamycin. Fraley et al., *Proc. Natl. Acad. Sci. USA*, 80:4803 (1983). Another commonly used selectable marker gene is the hygromycin phosphotransferase gene which confers resistance to the antibiotic hygromycin. Vanden Elzen et al., *Plant Mol. Biol.*, 5:299 (1985).

Additional selectable marker genes of bacterial origin that confer resistance to antibiotics include gentamycin acetyl transferase, streptomycin phosphotransferase, aminoglycoside-3'-adenyl transferase, and the bleomycin resistance determinant. Hayford et al., *Plant Physiol.* 86:1216 (1988), Jones et al., *Mol. Gen. Genet.* 210:86 (1987), Svab et al., *Plant Mol. Biol.* 14:197 (1990), Hille et al., *Plant Mol. Biol.* 7:171 (1986). Other selectable marker genes confer resistance to herbicides such as glyphosate, glufosinate or bromoxynil. Comai et al., *Nature* 317:741–744 (1985), Gordon-Kamm et al., *Plant Cell* 2:603–618 (1990) and Stalker et al., *Science* 242:419–423 (1988).

Other selectable marker genes for plant transformation are not of bacterial origin. These genes include, for example, mouse dihydrofolate reductase, plant 5-enolpyruvylshikimate-3-phosphate synthase and plant acetolactate synthase. Eichholtz et al., *Somatic Cell Mol. Genet.* 13:67 (1987), Shah et al., *Science* 233:478 (1986), Charest et al., *Plant Cell Rep.* 8:643 (1990).

Commonly used genes for screening presumptively transformed cells include β-glucuronidase (GUS), β-galactosidase, luciferase, and chloramphenicol acetyltransferase. Jefferson, R. A., *Plant Mol. Biol. Rep.* 5:387 (1987)., Teeri et al., *EMBO J.* 8:343 (1989), Koncz et al., *Proc. Natl. Acad. Sci. USA* 84:131 (1987), De Block et al., *EMBO J.* 3:1681 (1984), green fluorescent protein (GFP) (Chalfie et al., *Science* 263:802 (1994), Haseloff et al., *TIG* 11:328–329 (1995) and PCT application WO 97/41228). Another approach to the identification of relatively rare transformation events has been use of a gene that encodes a dominant constitutive regulator of the *Zea mays* anthocyanin pigmentation pathway. Ludwig et al., *Science* 247:449 (1990).

Suitable selection markers for use in prokaryotes and eukaryotes other than plants are also well known. See, e.g., PCT WO 96/23898 and PCT WO 97/42320. For instance, resistance to antibiotics (ampicillin, kanamycin, tetracyline, chloramphenicol, neomycin or hygromycin) may be used as the selection marker.

According to another aspect of the present invention, tolerance to dicamba can be used as a selection marker for plants and plant cells. "Tolerance" means that transformed plant cells are able to grow (survive and regenerate into plants) when placed in culture medium containing a level of dicamba that prevents untransformed cells from doing so. "Tolerance" also means that transformed plants are able to grow after application of an amount of dicamba that inhibits the growth of untransformed plants.

Methods of selecting transformed plant cells are well known in the art. Briefly, at least some of the plant cells in a population of plant cells (e.g., an explant or an embryonic suspension culture) are transformed with a DNA construct according to the invention providing for dicamba degradation. The resulting population of plant cells is placed in culture medium containing dicamba at a concentration selected so that transformed plant cells will grow, whereas untransformed plant cells will not. Suitable concentrations of dicamba can be determined empirically as is known in the art.

Methods of selecting transformed plants are also known in the art. Briefly, dicamba is applied to a population of plants suspected of comprising a DNA construct according to the invention providing for dicamba degradation. The amount of dicamba is selected so that transformed plants will grow, and the growth of untransformed plants will be inhibited. The level of inhibition must be sufficient so that transformed and untransformed plants can be readily distinguished (i.e., inhibition must be statistically significant). Such amounts can be determined empirically as is known in the art.

Further, the generation of 3,6-DCSA as a result of the degradation of dicamba can be used for selection and screening. The generation of 3,6-DCSA can be readily ascertained by observing the fluorescence of this compound, allowing selection and screening of transformed host cells, intact organisms, and parts of organisms (e.g., microorganisms, plants, plant parts, and plant cells). In this regard, the invention allows for selection and screening of transformed host cells, intact organisms, and parts of organisms in the same manner as for green fluorescent protein (GFP). See U.S. Pat. Nos. 5,162,227 and 5,491,084 and PCT applications WO 96/27675, WO 97/11094, WO 97/41228 and WO 97/42320, all of which are incorporated herein by reference. In particular, 3,6-DCSA can be detected in transformed host cells, intact organisms, and parts of organisms using conventional spectrophotometric methods. For instance, microscopes can be fitted with appropriate filter combinations for fluorescence excitation and detection. A hand-held lamp may be used for benchtop work or field work (see Example 1). Fluorescence-activated cell sorting can also be employed. 3,6-DCSA is excited at a wavelength of 312–313 nm, with a maximum emission wavelength of 424 nm.

"Parts" of organisms include organs, tissues, or any other part. "Plant parts" include seeds, pollen, embryos, flowers, fruits, shoots, leaves, roots, stems, explants, etc.

Selection based on dicamba tolerance or dicamba degradation can be used in the production of dicamba-tolerant plants or dicamba-degrading microorganisms, in which case the use of another selection marker may not be necessary. Selection based on dicamba tolerance or dicamba degradation can also be used in the production of transgenic cells or organisms that express other genes of interest. Many such genes are known and include genes coding for proteins of commercial value and genes that confer improved agronomic traits on plants (see, e.g., PCT WO 97/41228, the complete disclosure of which is incorporated herein by reference).

The DNA constructs of the invention can be used to transform a variety of host cells, including prokaryotes and eukaryotes. The DNA sequences coding for the dicamba-degrading enzyme(s) and the selection marker, if a separate selection marker is used, may be on the same or different DNA constructs. Preferably, they are arranged on a single DNA construct as a transcription unit so that all of the coding sequences are expressed together. Also, the gene(s) of interest and the DNA sequences coding for the dicamba-degrading enzyme(s), when dicamba-tolerance or dicamba degradation is being used as a selection marker, may be on the same or different DNA constructs. Such constructs are prepared in the same manner as described above.

Suitable host cells include prokaryotic and eukaryotic microorganisms (e.g., bacteria (including *Agrobacterium tumefaciens* and *Escherichia coli*), yeast (including *Saccharomyces cerevisiae*) and other fungi (including *Aspergillus* sp.), plant cells, insect cells, and mammalian cells. Preferably, the host cell is one that does not normally degrade dicamba. However, the present invention can also be used to increase the level of dicamba degradation in host cells that normally degrade dicamba.

Thus, the "transgenic" cells and organisms of the invention include cells and organisms that do not normally degrade dicamba, but which have been transformed according to the invention so that they are able to degrade this herbicide. The "transgenic" cells and organisms of the invention also include cells and organisms that normally degrade dicamba, but which have been transformed according to the invention so that they are able to degrade more of this herbicide or to degrade the herbicide more efficiently.

Methods of transforming prokaryotic and eukaryotic host cells are well known in the art. See, e.g., Maniatis et al., *Molecular Cloning: A Laboratory Manual*, Cold Spring Harbor, N.Y. (1982), Sambrook et al., *Molecular Cloning: A Laboratory Manual*, Cold Spring Harbor, N.Y. (1989); PCT WO 96/23898 and PCT WO 97/42320.

For instance, numerous methods for plant transformation have been developed, including biological and physical transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc., Boca Raton, 1993) pp. 67–88. In addition, vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pp. 89–119.

The most widely utilized method for introducing an expression vector into plants is based on the natural transformation system of *Agrobacterium*. See, for example, Horsch et al., Science 227:1229 (1985). *A. tumefaciens* and *A. rhizogenes* are plant pathogenic soil bacteria which genetically transform plant cells. The Ti and R1 plasmids of *A. tumefaciens* and *A. rhizogenes*, respectively, carry genes responsible for genetic transformation of the plant. See, for example, Kado, C. I., *Crit. Rev. Plant. Sci.* 10:1 (1991). Descriptions of *Agrobacterium* vector systems and methods for *Agrobacterium*-mediated gene transfer are provided by numerous references, including Gruber et al., supra, Miki et al., supra, Moloney et al., *Plant Cell Reports* 8:238 (1989), and U.S. Pat. Nos. 4,940,838 and 5,464,763.

A generally applicable method of plant transformation is microprojectile-mediated transformation wherein DNA is carried on the surface of microprojectiles. The expression vector is introduced into plant tissues with a biolistic device that accelerates the microprojectiles to speeds sufficient to penetrate plant cell walls and membranes. Sanford et al., *Part. Sci. Technol.* 5:27 (1987), Sanford, J. C., *Trends Biotech.* 6:299 (1988), Sanford, J. C., *Physiol. Plant* 79:206 (1990), Klein et al., *Biotechnology* 10:268 (1992).

Another method for physical delivery of DNA to plants is sonication of target cells. Zhang et al., *Bio/Technology* 9:996 (1991). Alternatively, liposome or spheroplast fusion have been used to introduce expression vectors into plants. Deshayes et al., *EMBO J.*, 4:2731 (1985), Christou et al., *Proc Natl. Acad. Sci. USA* 84:3962 (1987). Direct uptake of DNA into protoplasts using $CaCl_2$ precipitation, polyvinyl alcohol or poly-L-ornithine have also been reported. Hain et al., *Mol. Gen. Genet.* 199:161 (1985) and Draper et al., *Plant Cell Physiol.* 23:451 (1982). Electroporation of protoplasts and whole cells and tissues have also been described. Donn et al., In Abstracts of VIIth International Congress on Plant Cell and Tissue Culture IAPTC, A2-38, p. 53 (1990); D'Halluin et al., *Plant Cell* 4:1495–1505 (1992) and Spencer et al., *Plant Mol. Biol.* 24:51–61 (1994).

Transgenic dicamba-tolerant plants of any type may be produced according to the invention. In particular, broadleaf plants (including beans, soybeans, cotton, peas, potatoes, sunflowers, tomatoes, tobacco, fruit trees, and ornamental plants and trees) that are currently known to be injured by dicamba can be transformed so that they become tolerant to the herbicide. Other plants (such as corn, sorghum, small grains, sugarcane, asparagus, and grass) which are currently considered tolerant to dicamba can be transformed to increase their tolerance to the herbicide. "Tolerant" means that the transformed plants can grow in the presence of an amount of dicamba which inhibits the growth of untransformed plants.

It is anticipated that the dicamba-degrading oxygenases of the invention can function with endogenous reductases and ferredoxins found in transgenic host cells and organisms to degrade dicamba. Plant chloroplasts are particularly rich in reductases and ferredoxins. Accordingly, a preferred embodiment for the production of transgenic dicamba-tolerant plants is the use of a sequence coding for peptide that will direct the dicamba-degrading oxygenase into chloroplasts ("a chloroplast targeting sequence"). DNA coding for the chloroplast targeting sequence is preferably placed upstream (5') of the sequence coding for the dicamba-degrading oxygenase, but may also be placed downstream (3') of the coding sequence, or both upstream and downstream of the coding sequence. Exemplary chloroplast targeting sequences include the maize cab-m7 signal sequence (see Becker et al., *Plant Mol. Biol.* 20:49 (1992) and PCT WO 97/41228) and the pea glutathione reductase signal sequence (Creissen et al., *Plant J.* 2:129 (1991) and PCT WO 97/41228). An alternative preferred embodiment is the direct transformation of chloroplasts using a construct comprising a promoter functional in chloroplasts to obtain expression of the oxygenase in chloroplasts. See, e.g., PCT application WO 95/24492 and U.S. Pat. No. 5,545,818.

In yet another embodiment, the invention provides a method of controlling weeds in a field where transgenic dicamba-tolerant plants are growing. The method comprises applying an effective amount of dicamba to the field to control the weeds. Methods of applying dicamba and amounts of dicamba effective to control various types of weeds are known. See *Crop Protection Reference*, pages 1803–1821 (Chemical & Pharmaceutical Press, Inc., New York, N.Y., 11th ed., 1995).

In another embodiment, the invention provides a method of degrading dicamba present in a material, such as soil, water, or waste products of a dicamba manufacturing facility. Such degradation can be accomplished using the dicamba-degrading enzymes of the invention. The enzymes can be purified from microorganisms naturally expressing them (see Example 1) or can be purified from transgenic host cells producing them. If the enzymes are used in such methods, then appropriate cofactors must also be provided (see Example 1). Effective amounts can be determined empirically as is known in the art (see Example 1). Alternatively, transgenic prokaryotic and eukaryotic microorganisms can be used to degrade dicamba in such materials. Transgenic prokaryotic and eukaryotic microorganisms can be produced as described above, and effective amounts can be determined empirically as is known in the art.

Dicamba is introduced into the environment in large quantities on a continuing basis. The elimination of dicamba is dependent in large part on the action of enzyme systems which are found in microorganisms inhabiting the soil and water of the planet. An understanding of these enzyme systems, including dicamba-degrading O-demethylases and their three components, is important in efforts to exploit natural and genetically modified microbes for bioremediation and the restoration of contaminated soil, water and other materials. Thus, the dicamba-degrading enzymes, DNA molecules, DNA constructs, etc., of the invention can be used as research tools for the study of dicamba degradation and bioremediation.

Finally, the dicamba-degrading enzymes of the invention can be used in an assay for dicamba. A sample suspected of containing dicamba is mixed with a dicamba-degrading O-demethylase or a combination of a dicamba-degrading oxygenase, a dicamba-degrading ferredoxin and a dicamba-degrading reductase. Suitable assays are described in Example 1. In particular, detecting or quantitating the fluorescence due to the generation of 3,6-DCSA makes for a convenient assay.

EXAMPLES

Example 1

Purification And Characterization Of The Components Of Dicamba O-Demethylase Of *Pseudomonas maltophilia* DI-6

Methods and Materials:

Bacterium and growth conditions. *Pseudomonas maltophilia*, strain DI-6 (Kreuger, et al., (1989) *J. Agric. Food Chem.*, 37:534–538) was isolated from a soil site persistently contaminated with dicamba. The bacterium was provided by Dr. Douglas Cork of the Illinois Institute of Technology (Chicago, Ill.), and was maintained on reduced chloride medium (Kreuger, J. P., (1989) Ph.D. thesis, Illinois Institute of Technology, Chicago, Ill.), supplemented with either dicamba (2 mg/ml) or a mixture of glucose (2 mg/ml) and Casamino Acids (2 mg/ml). The carbon sources were filter-sterilized and added to the medium after it was autoclaved. Solid media were prepared by the addition of 1% (wt/vol) Gelrite (Scott Laboratories, West Warwick, R. I.).

Chemicals and reagents. Dicamba, 3,6-DCSA, and [$^{14}$C] dicamba (U-phenyl-$^{14}$C, 42.4 mCi/mmol, radiochemical purity greater than 98%) were supplied by Sandoz Agro, Inc. (Des Plaines, Ill.). To increase solubility, the dicamba and 3,6-DCSA stock solutions were prepared by titration with KOH to pH 7.0. All chemicals were purchased from Sigma Chemical Co. (St. Louis, Mo.), unless otherwise stated. Superose 12, Mono Q, Q-Sepharose (Fast Flow) and Phenyl-Sepharose (CL-4B) column packings for the FPLC (fast performance liquid chromatography) apparatus were obtained from Pharmacia (Milwaukee, Wis.). Ampholyte pH 4-6 and ampholyte pH 4-9 were purchased from Serva (Heidelberg, FRG). Acrylamide, β-mercaptoethanol, N,N,N',N'-tetramethylethylenediamine (TEMED) and ammonium persulfate (APS) were from Bio-Rad Laboratories (Hercules, Calif.). Thin layer chromatography (TLC) plates were silica gel (250 μm thickness) with UV 254 indicator, and were purchased from J. T. Baker Chemical Co. (Phillipsburg, N.J.).

Enzyme assays. Dicamba O-demethylase activity was assayed by measuring the formation of [$^{14}$C]3,6-DCSA from [$^{14}$C] dicamba. Briefly, the activity in mixtures of enzyme components was measured at 30° C. in a standard 300 μl reaction mixture containing 25 mM potassium phosphate buffer (pH 7.0), 10 mM $MgCl_2$, 0.5 mM NADH (beta-nicotinamide adenine dinucleotide, reduced form), 0.5 mM ferrous sulfate, 50 μM cold dicamba, 2.5 μM [$^{14}$C] dicamba (the final specific activity of the radioactive dicamba was 1.9 mCi/mmol), and different amounts of cell lysate or partially purified enzyme. All enzyme assays during the final purification steps were conducted in phosphate buffer because the pH optimum for dicamba O-demethylase activity was found to be in the mid range of phosphate buffers, and higher enzyme activity was observed with phosphate buffer compared to Tris-HCl [tris(hydroxymethyl)aminomethane hydrochloride] buffer at pH 7.0. Reactions were initiated by the addition of the substrate, dicamba. At specific times, the reactions were stopped by adding 50 μl of 5% (vol/vol) $H_2SO_4$. Dicamba and dicamba metabolites were then extracted twice with one volume of ether, and the extracts were evaporated to dryness. The efficiencies of recovery (means±standard deviations) for the extraction procedure were 87%±2% for dicamba and 85%±3% for 3,6-DCSA (Yang et al., *Anal. Biochem.* 219:37–42 (1994)).

[$^{14}$C] dicamba and $^{14}$C-labeled metabolites were separated by thin layer chromatography (TLC). The ether-extracted dicamba and its metabolites were redissolved in 50 μl of ether prior to being spotted onto a TLC plate. The solvent system for running the TLC was chloroform-ethanol-acetic acid (85:10:5 [vol/vol/vol]). The resolved reaction products were visualized and quantified by exposing the TLC plate to a phosphor screen for 24 hours and then scanning the screen in a PhosphorImager SF (Molecular Dynamics, Sunnyvale, Calif.). Estimates of the amount of radioactivity in a particular spot on the TLC plate were determined by comparing the total pixel count in that spot relative to a spot on the same plate containing a known amount of [$^{14}$C] dicamba. One unit of activity was defined as the amount of enzyme that catalyzes the formation of 1 nmol of 3,6-DCSA from dicamba per minute at 30° C. Specific activities were based on the total protein concentration of the assay mixture.

The activity of the reductase component of dicamba demethylase was assayed by measuring reduction of 2,6-dichlorophenolindophenol (DCIP) with a Hitachi U-2000 spectrophotometer. The reaction contained 0.5 mM NADH, 0.2 mM FAD (flavin adenine dinucleotide), 50 μmM DCIP, 20 mM Tris buffer (pH 8.0), and 10–100 μl of enzyme sample in a total volume of 1 ml. The change in absorbance at 600 nm with time was measured at room temperature. Specific activity was calculated using an extinction coefficient at 600 nm of 21.0 $mM^{-1}$ $cm^{-1}$ for reduced DCIP. Specific activity was expressed as nmol DCIP reduced $min^{-1}$ $mg^{-1}$ of protein.

In addition, an in situ DCIP assay was used to detect and locate the reductase activity in protein preparations separated on isoelectric focusing (IEF) gels. After electrophoresis of the proteins on an IEF gel, lanes sliced from the gel were washed with 20 ml of cold 20 mM Tris-HCl buffer (pH 8.0). Low melting agarose was dissolved by heating in 10 ml of 20 mM Tris-HCl buffer (pH 8.0) at a final concentration of 1.5% (w/v). When the agarose cooled to near room temperature, it was supplemented with 0.2 mM FAD, 50 μM DCIP, and 0.5 mM NADH. The assay mixture was poured onto a glass plate and allowed to solidify. The gel piece was placed on top of the solidified reaction mixture and allowed to set at room temperature for 15 minutes. If the gel slice contained a protein with reductase activity, a colorless band of reduced DCIP was generated in the blue background of DCIP.

Cell lysates. Cells were grown to an optical density at 550 nm of 1.3 to 1.5 in liquid reduced chloride medium containing a mixture of glucose and Casamino Acids on a rotary shaker (250 rpm at 30° C.). The cells were harvested by centrifugation, washed twice with cold 100 mM $MgCl_2$, and centrifuged again. Cell pastes were either used immediately or quickly frozen in liquid nitrogen and stored at –80° C. At the time of enzyme purification, 25 g of frozen cells were thawed and resuspended in 50 ml of isolation buffer containing 25 mM Tris buffer (pH 7.0), 10 mM $MgCl_2$, and 0.5 mM EDTA. Phenylmethylsulfonyl fluoride and dithiothreitol were added to final concentrations of 0.5 mM and 1 mM, respectively. After addition of 10 mg of lysozyme and 1 mg of DNase, cells were stirred for 10 min on ice and broken by sonication (model XL2020 sonicator; Heat Systems) on ice at a medium setting (setting 5) with twelve 20-second bursts and 40-second resting intervals. The resulting cell lysates were diluted to 90 ml with isolation buffer and centrifuged at 76,000×g for 1 h at 4° C. The supernatant was used as the source of cleared cell lysate.

Enzyme purification. All procedures were performed at 4° C., unless otherwise stated. Solid ammonium sulfate was slowly added to a 90-ml volume of cleared cell lysate to 40% (wt/vol) saturation, with constant stirring. After 15 minutes of stirring, the mixtures were centrifuged at 15,400×g for 15 minutes, and the precipitate was discarded. Additional solid ammonium sulfate was added to 70% (wt/vol) saturation, with constant stirring of the supernatant. After 15 min of stirring, the mixtures were centrifuged under the conditions described above. The supernatant was discarded, and the precipitate was resuspended in a minimal volume of buffer A (20 mM Tris [pH 8.0], 2.5 mM $MgCl_2$, 0.5 mM EDTA, 5% (vol/vol) glycerol, and 1 mM dithiothreitol).

The 40%–70% ammonium sulfate cut was then loaded onto a Phenyl-Sepharose column (2.5 by 10 cm) connected to a FPLC apparatus (Pharmacia) and eluted with a decreasing linear gradient of $(NH_4)_2SO_4$ from 10% (w/v) to 0% (w/v). The column was preequilibrated with buffer A containing 10% (wt/vol) ammonium sulfate. The flow rate was 1 ml/min. Protein concentrations were continuously monitored at $A_{280}$ during column elution. The column was washed with 120 ml of buffer A containing 10% (wt/vol) ammonium sulfate until baseline $A_{280}$ readings were obtained. Bound proteins were eluted with a decreasing gradient of $(NH_4)_2SO_4$ in buffer A [10 to 0% (wt/vol) $(NH_4)_2SO_4$ in a total volume of 210 ml]. Fractions of 2 ml were collected. Aliquots of 10 µl were taken from each fraction and added to the standard dicamba O-demethylase assay mixture (see above), except that nonradioactive dicamba was used as the substrate. Dicamba O-demethylase activity was detected by monitoring the conversion of dicamba to the highly fluorescent reaction product 3,6-DCSA with a hand-held UV lamp (312 nm, Fotodyne) in a darkened room.

This procedure allowed resolution of dicamba O-demethylase into three pools containing the separated components (designated components I, II and III). Each component was essential for dicamba O-demethylase activity (see below). When a single component was assayed, the other two components were provided in excess. Fractions containing a single type of activity were pooled (component I, fractions 128–145; component II, unbound fractions 12–33; component III, fractions 62–92).

(i) Purification of component I. Fractions containing component I activity (eluting from a Phenyl-Sepharose column at 0 M $(NH_4)_2SO_4$, fractions 128–145) were pooled to provide a total volume of 34 ml. The pooled samples were concentrated to 10 ml by centrifugation in a Centriprep-10 device (Amicon) and then applied to a Q-Sepharose (Fast Flow) FPLC column (Pharmacia) (2.5 by 6 cm) equilibrated with buffer A and washed with 80 ml of buffer A. Proteins bound to the column were eluted with a 100 ml linear gradient of 0 to 0.6 M KCl in buffer A at a flow rate of 1 ml/min. Fractions were collected at 1.5 minute intervals. Those fractions exhibiting component I activity (fractions 29–37) were pooled, dialyzed against buffer A overnight at 4° C. and applied to a Mono Q HR 5/5 FPLC anion-exchange column in buffer A. Proteins were eluted at 1 ml/min by using a 50 ml gradient of increasing KCl concentration (0 to 0.5 M). Fractions showing component I activity (fractions 19 to 25) were pooled and concentrated to 0.4 ml by centrifugation in a Centricon-10 device. The concentrated sample was then subjected to chromatography on a Superose 12 FPLC column (1.6 by 50 cm) at a flow rate of 0.2 ml/min with buffer A containing 100 mM KCl. Fractions 7–10 showing component I activity were pooled and concentrated by centrifugation in a Centricon-10 device.

The partially purified component I was diluted with cold 1% (w/v) glycine and concentrated by centrifugation in a Centricon-10 device three more times to desalt it in preparation for IEF electrophoresis. The desalted and concentrated sample was then applied to a 6% (w/v) IEF (pH 4–6) gel and subjected to electrophoresis for 1.5 hours at 4° C. (see below). After electrophoresis, the gel was washed with 25 mM cold phosphate buffer (pH 7.0) for 5 minutes and then each slice of the gel lane was diced into small (6 mm×4 mm) pieces. Protein was eluted from the diced gel fragments by grinding them with a pipette tip in the presence of 10 µl of 25 mM phosphate buffer (pH 7.0). Protein from each segment was mixed with an excess of components II and III and assayed for dicamba O-demethylase activity. The gel segment which showed component I activity (which was also reddish brown in color) was loaded onto a 12.5% (w/v) sodium dodecyl sulfate polyacrylamide gel (SDS-PAGE) to check sample purity.

(ii) Purification of component II. Component II obtained by Phenyl-Sepharose column chromatography was dialyzed against buffer A overnight at 4° C. and applied to a FPLC Q-Sepharose column (2.5 by 6 cm). Sample elution conditions were identical to those described above for component I except that the elution gradient was 0 to 1 M KCl in buffer A. Fractions exhibiting component II activity (fractions 30–37) were pooled, dialyzed against buffer A, concentrated to 0.4 ml and applied to a FPLC Superose 12 column (1.6 by 50 cm). The procedures for sample application and elution were identical to those described above for component I. Fractions exhibiting component II activity (fractions 3–6) were pooled, diluted with an equal volume of buffer A, and applied to a FPLC Mono Q column. Proteins were eluted from the column using the same KCl gradient as for component I. Fractions 20–25 showed component II activity. Partially purified component II was further purified by IEF (pH 4–6) electrophoresis using the same conditions as described for component I. The gel segment which showed component II activity was loaded onto a 12.5% (w/v) SDS-PAGE for further analysis.

(iii) Purification of component III. Component III obtained by Phenyl-Sepharose column chromatography was dialyzed against buffer A overnight at 4° C. and applied to a FPLC Q-Sepharose column (2.5 by 6 cm). Conditions were identical to those described above for component I. Fractions exhibiting component III activity (fractions 26–38) were dialyzed against buffer B [10 mM Tris-HCl (pH 7.5), 2.5 mM $MgCl_2$, 5% (v/v) glycerol, 1 mM dithiothreitol] and concentrated to 5 ml. Blue dye affinity matrix [Cibacron Blue 3GA type 3000 (Sigma)] was packed into a FPLC column (1×5 cm) and pre-equilibrated with 20 ml of buffer B. Concentrated component III was loaded onto the blue dye column and washed with 20 ml of buffer B at a flow rate of 0.2 ml/min until the $A_{280}$ of the column effluent reached baseline levels. Bound protein was then eluted with 5 mM NADH in buffer B. Fractions containing reductase activity were detected by assaying for dicamba O-demethylase activity in the presence of an excess of components I and II and also by the ability of each fraction to reduce DCIP in the presence of NADH. Fractions having strong reductase activity in both assays were pooled, dialyzed against buffer A containing 100 mM KCl, concentrated to 0.2 ml, and applied to a FPLC Superose 12 column. The same conditions were used for running the Superose column as described for component I. Fractions containing proteins which catalyzed DCIP reduction were pooled, dialyzed against buffer A and applied to a FPLC Mono Q column. Proteins were eluted using the same conditions as for component I. Partially purified component III was further purified by IEF (pH 4–6) gel electrophoresis. The reductase activity of proteins within the IEF gel was detected by assaying for DCIP reduction in an agarose gel overlay as described above. The gel segment which showed component II activity was loaded onto a 12.5% (w/v) SDS-PAGE for further analysis.

Determination of $NH_2$-terminal amino acid sequences. Protein bands identified on IEF gels as having component I, component II, or component III activities were excised and placed in the wells of a 12.5% (w/v) SDS polyacrylamide gel. After electrophoresis, the gel slices containing the purified proteins were transblotted onto a PVDF (polyvinylidene difluoride) membrane (Millipore) in a Trans-Blot cell (Bio-Rad, Richmond, Calif.) at 25 volts for 16 hours. The blotting buffer was a solution of 20% (v/v) methanol with 10 mM CAPS [3-(cyclohexylamino)-1-propanesulfonic acid], pH 10.0. Sequencing was performed using an Applied Biosystems Inc. 420H machine by Edman degradation (Edman and Henschen (1975) pages 232–279 in S. B. Needleman (ed.), Protein sequence determination, 2nd ed., Springer-Verlage, New York).

Determination of protein concentration. Protein concentrations were determined by the method of Bradford (1976) *Anal. Biochem.* 72:248–254, with bovine serum albumin as the standard.

SDS-PAGE. Sodium dodecyl sulfate-polyacrylamide gel eletrophoresis (SDS-PAGE) was performed according to modified methods of Laemmli (Laemmli (1970) *Nature*, 227:680–685). 12.5% (w/v) SDS gels of 85×65×0.75 mm were made as follows: running gel: 2.5 ml 40% (w/v) acrylamide/bis solution (37:5:1), 1 ml running buffer solution [3M Tris-HCl (pH 8.8), 0.8% (w/v) SDS], 4.5 ml $H_2O$, 5 µl TEMED, and 40 µl 10% (w/v) APS; stacking gel: 0.5 ml 40% (w/v) acrylamide/bis, 0.5 ml stacking buffer solution [1 M Tris-HCl (pH 6.8), 0.8% (w/v) SDS], 3 ml $H_2O$, 5 µl TEMED, and 12.5 µl 10% (w/v) APS. The composition of the running buffer was 25 mM Tris-HCl (pH 8.3), 0.2 M glycine, and 0.1% (w/v) SDS. The sample buffer contained 0.25 ml stacking buffer, 0.6 ml 20% (w/v) SDS, 0.2 ml β-mercaptoethanol, and 0.95 ml 0.1% bromphenol blue (w/v) in 50% (v/v) glycerol. Electrophoresis was performed at 80 volts in a Bio-Rad Mini Gel apparatus until the tracking dye was 0.5 cm from the anode end of the gel. Proteins were stained with 0.1% (w/v) Coomassie Brilliant Blue R-250 in a mixture of isopropanol, water, and acetic acid at a ratio of 3:6:1 (v/v/v). Destaining was performed in a mixture of methanol, water, and acetic acid at a ratio of 7:83:10 (v/v/v). Standard proteins (Gibco BRL) included: myosin (214.2 kDa), phosphorylase B (111.4 kDa), bovine serum albumin (74.25 kDa), ovalbumin (45.5 kDa), carbonic anhydrase (29.5 kDa), β-lactoglobulin (18.3 kDa), and lysozyme (15.4 kDa).

Determination of molecular weight. The molecular weight ($M_r$) of peptides under denaturing conditions was estimated using SDS-PAGE analysis. The molecular weights of the native components I, II and III were estimated by gel filtration through a Superose 12 HR 10/30 FPLC column (Pharmacia) at a flow rate of 0.2 ml/min in buffer A containing 100 mM KCl. Calibration proteins were gel filtration standards from Bio-Rad. They were: bovine thyroglobulin (670 kDa), bovine gamma globulin (158 kDa), chicken ovalbumin (44 kDa), horse myoglobin (17 kDa) and vitamin B-12 (1.35 kDa). The void volume of the Superose 12 column was calculated using Blue Dextran ($M_r$ 2,000,000, Sigma).

IEF. Isoelectric focusing (IEF) gel electrophoresis was performed in a vertical mini-gel apparatus (Model #MGV-100) from C.B.S. Scientific Co. (Del Mar, Calif.). IEF gels with 6% (w/v) polyacrylamide (70×90×1 mm) were made by mixing the following: 1.6 ml 30% (w/v) acrylamide/bis (37:5:1), 0.8 g glycerol, 0.32 ml ampholyte pH 4–6 (Serva), 0.08 ml ampholyte pH 4–9 (Serva), 5.2 ml $H_2O$, 10 µl TEMED, and 80 µl 10% (w/v) APS. The cathode buffer was 100 mM β-alanine and the anode buffer was 100 mM acetic acid. Protein samples in approximately 1 to 10 µl of 1% (w/v) glycine were mixed with an equal volume of sample buffer [50% (v/v) glycerol, 1.6% (v/v) ampholyte pH 4–9, 2.4% (v/v) ampholyte pH 4–6]. Samples were loaded at the cathode end of the gel and allowed to migrate at 200 volts for 1.5 hours and 400 volts for another 1.5 hours. Proteins were stained with Coomassie Brilliant Blue R-250 using the procedure described above for SDS polyacrylamide gels. IEF markers (Sigma) were: amyloglucosodase, pI 3.6; glucose oxidase, pI 4.2; trypsin inhibitor, pI 4.6; β-lactoglobulin A, pI 5.1; carbonic anhydrase II, pI 5.4; carbonic anhydrase II, pI 5.9 and carbonic anhydrase I, pI 6.6 Kinetic analysis. The kinetics of the demethylation reaction catalyzed by dicamba O-demethylase were studied by analyzing the initial rates of the reaction in the presence of a constant concentration of the enzyme and increasing concentrations of the substrate, dicamba. Reaction mixtures contained 25 mM potassium phosphate buffer (pH 7.0), 10 mM $MgCl_2$, 0.5 mM NADH, 0.5 mM $FeSO_4$, 25 µg of partially purified O-demethylase enzyme [the 40%–70% (w/v) $(NH_4)_2SO_4$ fraction from a cleared cell lysate], various concentrations (0.5 to 50 µm) of dicamba and various concentrations (0.025 to 2.5 µM) of [$^{14}$C] dicamba (U-phenyl-14C, 42.4 mCi/mmol) in a total volume of 300 µl. For assays with dicamba concentrations of 0.5 µM and 1 µM, the reaction volume was increased to 900 µl to ensure that sufficient amounts of radioactive dicamba and its metabolites were present to allow detection. In these reactions, the amounts of all other components in the reaction were tripled. The conversion of [$^{14}$C] dicamba to [$^{14}$C]3,6-DCSA was determined for different time points at each concentration of dicamba using a PhosphorImager SF to scan radioactivity on phosphor screens which had been exposed to TLC plates for 24 hours. One unit of activity was defined as the amount of enzyme that forms 1 nmol of 3,6-DCSA per minute at 30° C. The initial rates of each reaction were determined by plotting the reaction rate versus time at each substrate concentration. Data were modeled to Michaelis-Menten kinetics and values of $K_m$ and $V_{max}$ were determined by fitting to Lineweaver-Burk plots using SigmaPlot® (Jandel Scientific, Corte Madera, Calif.).

Oxygen requirement. Preliminary experiments using a Clark oxygen electrode indicated oxygen consumption during a standard dicamba O-demethylase assay with dicamba as a substrate. To verify a requirement for oxygen in the 0 demethylation of dicamba by dicamba O-demethylase, reactions were conducted in an anaerobic chamber which contained less than 1 ppm of oxygen. The procedures for displacement of oxygen from the reaction mixture were performed at 4° C. Reaction mixtures lacking enzyme were placed in a vial and sealed with a rubber stopper. For displacement of oxygen, the vial was evacuated twice by vacuum and flushed each time with nitrogen. After a third evacuation, the vial was flushed with 90% nitrogen plus 10% hydrogen. The enzyme solution was likewise purged of oxygen (with care taken not to bubble the enzyme solution). Both the reaction mixtures and enzyme solutions were transferred into an anaerobic chamber (95% $N_2$-5% $H_2$ atmosphere). Two hundred forty microliters of cleared cell lysate was injected through the rubber stopper with a microsyringe and gently mixed with 960 µl of oxygen-free reaction mixture. Reactions were carried out at 30° C.

An examination of the reaction products on TLC plates showed that the rate of [$^{14}$C]3,6-DCSA production from [$^{14}$C] dicamba under anaerobic conditions was significantly lower than the rate of reactions with the same amount of enzyme under aerobic conditions. Under anaerobic conditions, there was virtually no conversion of dicamba to 3,6-DCSA within 1 hour. However, when a parallel reaction mixture was taken from the anaerobic chamber after 30 min and incubated with air, a significant quantity of one of the components of the dicamba O-demethylase enzyme complex was an oxygenase.

It may be noted that the in vitro conversion of [$^{14}$C] dicamba to [$^{14}$C]3,6-DCSA mimics the in vivo conversion pathway documented earlier (Cork and Kreuger, *Adv. Appl. Microbiol.* 36:1–66 (1991); Yang et al., *Anal. Biochem.* 219:37–42 (1994)). In these studies, DCSA was identified as a reaction product by both TLC and capillary electrophoresis. Stringent identification of the first major product of dicamba degradation as DCSA both in vivo and in vitro has been obtained by gas chromatography-mass spectrometry analyses.

Component and cofactor requirements. After the initial separation of the three components of dicamba O-demethylase by phenyl-Sepharose column chromatography, the partially purified preparations were taken individually through one additional purification on a Q-Sepharose column (2.5 by 6 cm). Samples were applied to a Q-Sepharose (Fast Flow) fast protein liquid chromatography column (Pharmacia) in buffer A and eluted with a 100-ml linear gradient of 0 to 0.6 M KCl (for the oxygenase component) or 0 to 1.0 M KCl (for the ferredoxin and reductase components) in 1.5-ml fractions. Appropriate pooled fractions from separate columns for oxygenase purification (fractions 29 to 37), for ferredoxin purification (fractions 30 to 37), or for reductase purification (fractions 26 to 38) were used for the determination of component and cofactor requirements.

The three components were assay for O-demethylase activity in various combinations to determine component requirements.

To determine cofactor requirements, O-demethylase activity was assayed using a mixture of the three components with [$^{14}$C] dicamba for 30 minutes at 30° C. The amounts of partially purified protein (provided in an optimized ratio) in the reaction mixtures were 85 µg of oxygenase, 55 µg of ferredoxin and 50 µg of reductase. The concentration of cofactors used in the reaction mixtures were 0.5 mM NADH, 0.2 mM FAD, 0.5 mM FeSO$_3$, 10 mM MgCl$_2$, 0.5 mM NADPH, and 0.2 mM FMN.

Results

Component I. The component of dicamba O-demethylase which bound most tightly to the Phenyl-Sepharose column (designated initially as component I and subsequently identified as an oxygenase) was distinctly reddish brown in color. This indicated the potential presence of a protein(s) containing an iron-sulfur cluster(s) or a heme group(s). The fractions with component I activity from the Phenyl-Sepharose column were subjected to further purification by Q-Sepharose (Fast Flow) and Mono Q chromatography and then to separation on a Superose 12 size exclusion column. The component I protein was then further purified on an IEF gel.

Protein from the major band on the IEF gel (with an apparent pI of approximately 4.6) was excised and separated from any remaining minor contaminants by SDS-PAGE. The major component I protein obtained after purification by IEF was greater than 90% pure as judged by densitometric analysis of this SDS-polyacrylamide gel stained with Coomassie Blue.

The N-terminal amino acid sequence of the dominant protein with an apparent molecular mass of approximately 40,000 Daltons was determined. Results of amino acid sequencing indicated that the first 29 amino acids of the N-terminal region were present in the following sequence (residues in parentheses are best guesses):

[SEQ ID NO:1]
Pro Thr Phe Val Arg Asn Ala Trp Tyr Val Ala Ala Leu

Glu Glu Leu Ser Glu Lys Pro Leu Gly Arg Thr Ile Leu

Asp (Asp or Thr) (Pro).

Comparison with amino acid sequences in various databases indicated little or no homology with NH$_2$-terminal sequences reported for other monoxygenases or dioxygeanses.

Component II. The protein fraction which did not bind to a Phenyl-Sepharose column was designated as component II. Because this yellowish colored fraction could be replaced by ferredoxin from *Clostridium pasteurianum* (but with slower reaction rates) when assays were performed in combination with components I and III, it was tentatively designated as a ferredoxin-containing fraction. The *Clostridium* ferredoxin clearly functioned in place of component II, but given the highly impure nature of the component II used in these experiments, the efficiency of the *Clostridium* enzyme was significantly lower than that of the putative ferredoxin from strain DI-6. In particular, 55 µg of partially purified component II mixed with excess amounts of components I and III catalyzed the conversion of dicamba to 3,6-DCSA at a rate of approximately 5 nmol min$^{-1}$ mg$^{-1}$, while 100 µg of highly purified ferredoxin from *Clostridium* resulted in an activity of only 0.6 nmol min$^{-1}$ mg$^{-1}$.

Purification steps involving Q-Sepharose (Fast Flow) chromatography, Superose 12 gel filtration and Mono Q chromatography yielded approximately one milligram of purified protein from an initial 25 grams of cell paste. This fraction was purified in a similar manner to the oxygenase component by electrophoresis on an IEF gel and subsequent electrophoresis of the active IEF fraction on an SDS-polyacrylamide gel.

Analysis of component II activity in proteins eluted from segments of the IEF gel indicated that a fraction with a pI of approximately 3.0 contained the active protein in component II. Protein from this gel slice was eluted and subjected to SDS-PAGE. Staining of the gel with Coomassie Blue revealed one prominent band of protein along with a smear of lower molecular weight proteins. The prominent protein with an apparent molecular weight of approximately 28,000 Daltons was blotted onto a PVDF membrane.

Amino acid sequencing revealed the following N-terminal sequence of 20 amino acids:

[SEQ ID NO:2]
Thr Tyr Val Val Thr Asp Ala Xaa Ile Lys Xaa Lys Tyr

Met Asp Xaa Val Glu Val Xaa.

Component III. Component III of dicamba O-demethylase was retained on a Phenyl-Sepharose column in high concentrations of $(NH_4)_2SO_4$ and eluted at approximately 4% (w/v) $(NH_4)_2SO_4$. This light yellow fraction was tentatively identified as a reductase-containing fraction based on its ability to reduce oxidized cytochrome c and DCIP in the presence of NADH and because it could be replaced by cytochrome c reductase from porcine heart (Type 1, Sigma) in assays with components I and II. In this set of reactions, the use of 50 µg of partially purified component III produced a reaction rate of approximately 5 nmol min$^{-1}$ mg$^{-1}$ when mixed with an excess of components I and II. The highly purified cytochrome c reductase showed a specific activity of approximately 2.5 nmol min$^{-1}$ mg$^{-1}$ in the reaction, an activity well below that provided by component III when one considers the impurity of the crude component III used in these assays. In addition, component III exhibited reductase activity when incubated with cytochrome c or 2,6-dichlorophenol-indophenol (DCPIP) in the presence of NADH. Neither component I nor component II showed activity in either of these two reductase assays.

Additional purification of this fraction by chromatography on columns containing Q-Sepharose (Fast Flow), blue dye affinity matrix, Superose 12, and Mono Q packings resulted in low amounts of protein in the fractions with reductase activity. The component III protein was about 70% pure as judged by densitometric analysis of the active protein fraction after separation by SDS-PAGE and staining with Coomassie Blue.

To further exacerbate purification of component III, it was found that two different protein fractions from the Mono Q column step contained reductase activity when assayed with the ferredoxin and oxygenase components. Further purification of these two fractions by eletrophoresis on an IEF gel revealed that the reductase activities of the two fractions had distinctly different isoelectric points. This was demonstrated by excising lanes containing each of the two reductase fractions from the IEF gel and laying the slices on top of a pad of low melt agarose containing a DCIP reaction mixture. Reductase activity in both gel slices was identified by the NADH-dependent reduction of DCIP to its colorless, reduced form. The reductase in fraction 35 had an apparent pI of approximately 5.6 while the reductase in fraction 27 possessed an apparent pI of approximately 4.8.

Both reductase activities isolated from the IEF gel slices were unstable and present in low amounts. Indeed, only the reductase from fraction 35 from the Mono Q column fractionation retained sufficient protein concentration and activity to allow further purification and characterization. A slice from an IEF gel containing this reductase activity was eluted and separated from contaminating proteins by SDS-PAGE. The predominant protein in this gel was one with a mass of approximately 45,000 Daltons. Size exclusion chromatography had indicated an approximate molecular mass of 50,000 Daltons for component III in its native state.

Biochemical characteristics of dicamba O-demethylase. Dicamba O-demethylase activity was measured during incubations in vitro at temperatures ranging from 20° C. to 50° C. and at pH values from approximately 6 to 9. Activity peaked sharply at 30° C. and broadly at pH values between 6.5 and 7.5. Enzymatic activity was dependent on the type of pH buffer employed. At pH 7, for example, activity was approximately 40% lower in Tris-containing buffers than in phosphate-containing buffers.

Values for $K_m$ and $V_{max}$ for dicamba O-demethylase were estimated using SigmaPlot® to generate best fit curves from Michaelis-Menten and Lineweaver-Burk plots of data from duplicate experiments. The $K_m$ for dicamba was estimated to be approximately 9.9±3.9 µM and the $V_{max}$ for the reaction was estimated to be approximately 108±12 nmol/min/mg.

The three components were assayed for dicamba O-demethylase activity in various combinations. None of the components showed enzyme activity when assayed alone. Indeed, a significant amount of O-demethylase activity could be detected only when all three components were combined. A mixture of components I and II exhibited small amounts of enzyme activity, probably due to traces of component III contaminating the component I fractions.

Both NADH and NADPH supported enzyme activity, with NADH being markedly more effective than NADPH. $Mg^{2+}$ was necessary for enzyme activity. $Fe^{2+}$, flavin adenine dinucleotide (FAD), and flavin mononucleotide (FMN) produced little or no stimulation of enzymatic activity with the partially purified protein preparations in these experiments. The highest activity was obtained using a combination of NADH, $Fe^{2+}$, $Mg^{2+}$, and FAD.

Discussion

Dicamba O-demethylase from *Pseudomonas* maltophilia, strain DI-6, is a three component oxygenase (Wang, X-Z (1996) Ph.D. thesis, University of Nebraska-Lincoln, Lincoln, Nebr.) responsible for the conversion of the herbicide, dicamba (2-methoxy-3,6-dichlorobenzoic acid), to 3,6-dichlorosalicylic acid (3,6-DCSA; 2-hydroxy-3,6-dichlorobenzoic acid). Purification schemes have been devised which have allowed the isolation of each of the three components to a homogeneous or near-homogeneous state.

Initial separation of the three components was achieved by chromatography on a Phenyl-Sepharose column. Enzymatic activities and other characteristics of the partially purified components allowed a tentative identification of the components as a reductase, a ferredoxin and an oxygenase—a composition similar to that found in a number of other previously studied heme-containing and nonheme-containing, multicomponent oxygenases (Batie, et al. (1992) pages 543–565, In F. Müller (ed.), *Chemistry and biochemistry of flavoenzymes*, vol. III, CRC Press, Boca Raton; Harayama, et al. (1992) *Annu. Rev. Microbiol.* 46:565–601; Mason and Cammack (1992) *Annu. Rev. Microbiol.* 46:277–305; Rosche et al. (1995) *Biochem. Biophys. Acta* 1252:177–179). Component III isolated from the Phenyl-Sepharose column catalyzed the NADH-dependent reduction of both cytochrome c and the dye, DCIP. In addition, its ability to support conversion of dicamba to 3,6-DCSA when combined with components I and II could be replaced in part by cytochrome c reductase. Component II could be replaced by the addition of ferredoxin from *Clostridium pasteurianum* to reactions containing components I and III. The absolute need for molecular oxygen to support the O-demethylation reaction indicated that the remaining component was an oxygenase.

Oxygenase$_{DIC}$. Component I of dicamba O-demethylase (designated as oxygenase$_{DIC}$) has been purified to homogeneity and subjected to N-terminal amino acid sequencing. The resulting sequence of twenty nine amino acid residues showed no significant homology to other protein sequences in the various data banks. However, the information obtained from this amino acid sequence permitted the design of degenerate oligonucleotide probes which have been successfully used to detect and clone the component I gene (see Example 2). Furthermore, a comparison of the amino acid sequence derived from the nucleotide sequence of this clone with that of the protein sequences in the data base showed strong homology to other oxygenases (see Example 2).

The apparent molecular mass of oxygenase$_{DIC}$, estimated from its migration in SDS-polyacrylamide gels, is approximately 40,000 Daltons. Purified preparations of the oxygenase exhibited only one major band on SDS-polyacrylamide gels stained with Coomassie Blue and Edman degradation of the protein contained in that band indicated the presence of only one N-terminal species. Estimates derived from the behavior of native oxygenase$_{DIC}$ on size exclusion columns suggests a molecular size of approximately 90,000 Daltons. All of these results suggest that the native oxygenase exists as a homodimer.

The oxygenase/hydroxylase component of a number of multicomponent systems is composed of an $(\alpha\beta)_n$-type subunit arrangement in which the larger $\alpha$ subunit is approximately 50,000 Daltons in size and the smaller $\beta$ subunit is approximately 20,000 Daltons in molecular mass (Harayama, et al. (1992) *Annu. Rev. Microbiol.* 46:565–601). In contrast, the oxygenase component of dicamba O-demethylase appears to possess a single subunit of approximately 40 kDa in molecular mass which may exist as a dimer in its native state. This $(\alpha)_n$-type subunit arrangement is similar to that found in other well characterized oxygenases such as 4-chlorophenylacetate 3,4-dioxygenase from *Pseudomonas* sp. strain CBS (Markus, et al. (1986) *J. Biol. Chem.* 261:12883–12888), phthalate dioxygenase from *Pseudomonas cepacia* Katie, et al. (1987) *J. Biol. Chem.* 262:1510–1518), 4-sulphobenzoate 3,4-dioxygenase from *Comamonas testosteroni* (Locher, et al. (1991) *Biochem. J.*, 274:833–842), 2-oxo-1,2-dihydroquinoline 8-monooxygenase from *Pseudomonas putida* 86 (Rosche et al. (1995) *Biochem. Biophys. Acta* 1252:177–179), 4-carboxydiphenyl ether dioxygenase from *Pseudomonas pseudoalcaligenes* (Dehmel, et al. (1995) *Arch. Microbiol.* 163:35–41), and 3-chlorobenzoate 3,4-dioxygenase from *Pseudomonas putida*, (Nakatsu, et al. (1995) *Microbiology* (Reading) 141:485–495).

Ferredoxin$_{DIC}$. Component II of dicamba O-demethylase (designated as ferredoxin$_{DIC}$) was purified to near homogeneity by several steps of column chromatography and IEF. Final purification by SDS-PAGE produced one major band of protein ($M_r \sim 28,000$) and a smear of slightly smaller proteins which may represent partial breakdown products of the purified ferredoxin.

A comparison of the N-terminal sequence of 20 amino acid residues obtained from the major protein band to other amino acid sequences in the various protein data banks using Genetics Computing Group (GCG) software package (University of Wisconsin, Madison, Wis.) revealed strong homology to a number of dicluster bacterial ferredoxins. For example, an alignment and comparison of the first 20 amino acids of ferredoxins from *Pseudomonas stutzeri, Pseudomonas putida, Rhodobacter capsulatus* and *Azotobacter vinelandii* showed these respective ferredoxins to have 65%, 65%, 65%, and 60% identity with the N-terminal sequence of the protein from *Pseudomonas maltophilia*, strain DI-6. The identity of the four residues designated in the putative ferredoxin sequence as Xaa was uncertain. Based on the position of the extra peaks on the chromatograph of the Edman degradation products, it is likely that these Xaa residues are actually propionyl-cysteine residues formed by the alkylation of the cysteine residues with acrylamide during SDS-PAGE (Brune (1992) *Anal. Biochem.* 207:285–290). If the four Xaa residues are all cysteine residues, the identities of the bacterial ferredoxin sequences with the ferredoxin from *Pseudomonas maltophilia* become 85%, 85%, 85%, and 80%, respectively.

The four dicluster ferredoxins which show strong homology to ferredoxin$_{DIC}$ have a [3Fe-4S] cluster followed by a [4Fe-4S] cluster at the N-terminus of the protein. This suggests that ferredoxin$_{DIC}$ is distinctly different from the ferredoxin components with [2Fe-2S] clusters which are usually associated with non-heme multicomponent oxygenases (Harayama, et al. (1992) *Annu. Rev. Microbiol.* 46:565–601; Mason and Cammack (1992) *Annu. Rev. Microbiol.* 46:277–305; Rosche, et al. (1995) *Biochem. Biophys. Acta* 1252:177–179). In fact, an analysis of the EPR (electron paramagnetic resonance) spectra [to be reported in detail elsewhere, Qiao, F., X-Z. Wang, P. L. Herman, D. P. Weeks, and J. H. Golbek (submitted for publication)] suggests that the [3Fe-4S] cluster at the N-terminus of ferredoxin$_{DIC}$ is the redox center which is active in electron transport.

Ferredoxin$_{DIC}$ is typical of other bacterial ferredoxins in having a low isoelectric point (i.e., a pI of 3 or slightly above). The low pI often leads to the aberrant migration of these proteins on SDS-polyacrylamide gels and during size exclusion chromatography (O'Keefe, et al. (1991) *Biochemistry* 30:447–455). In the case of ferredoxin$_{DIC}$, estimates of molecular mass based on migration of the protein during SDS-PAGE were approximately 28,000 Daltons. Likewise, size exclusion chromatography indicated an apparent molecular mass for the native ferredoxin$_{DIC}$ of approximately 28,000 daltons. This molecular mass is significantly higher than that of the other ferredoxins found in multicomponent oxygenases from bacteria [i.e., 8–13 kDa] (Batie, et al. (1992) pages 543–565, In F. Müller (ed.), Chemistry and biochemistry of flavoenzymes, vol. III, CRC Press, Boca Raton; Harayama, et al. (1992) *Annu. Rev. Microbiol.* 46:565–601).

Reductase$_{DIC}$. Component III of dicamba O-demethylase (designated as reductase$_{DIC}$) has been the most recalcitrant of the three components to purify. This is due in part to its apparent instability and low abundance in lysates of strain DI-6. Nonetheless, sufficient protein has been purified to assign a tentative molecular mass of 45,000 Daltons. This is similar to the molecular mass of approximately 50,000 Daltons obtained from size exclusion chromatography and suggests that reductase$_{DIC}$ exists in its native form as a monomer. The purification of the reductase component has been further complicated by the fact that chromatography on a Mono Q column and IEF resolves purified reductase preparations into two activities with apparently distinct pI values. Both fractions from the Mono Q column functioned in combination with purified ferredoxin$_{DIC}$ and oxygenase$_{DIC}$ to produce dicamba O-demethylase activity. The presence in *Sphingomonas* sp. strain RW1 of two similar flavoproteins which function equally well as reductase components in the three component dibenzofuran 4,4a-dioxygenase has recently been reported by Bünz and Cook (Bünz and Cook (1993) *J. Bacteriol.* 175:6467–6475). Interestingly, both reductases were 44,000 Daltons in molecular mass, quite similar to that of the 45,000 Dalton reductase$_{DIC}$. Multiple components of leghemoglobin reductase have also been observed in lupin root nodules using isoelectric focusing techniques (Topunov, et al. (1982) *Biokhimiya* (English edition) 162:378–379). In this case, IEF revealed four separate components with NADH-dependent reductase activity. The resolution of the question of whether there is only one reductase$_{DIC}$ which exists in two forms or two distinct reductases in strain DI-6 will rely on the development of improved procedures for isolating larger quantities of the proteins and/or on the cloning and sequencing of the gene(s) involved.

Dicamba O-demethylase characteristics. In addition to the physical and biochemical properties of the individual components noted above, analyses of enzymatic activity have shown that the O-demethylase system has a strong affinity ($K_m$=~10 μM) for its substrate and a $V_{max}$ of approximately 100–110 nmol/min/mg. As expected for a soil bacterium collected in a temperate climatic zone, the maximal enzymatic activity was observed at temperatures near 30° C. While the pH optima for the enzyme system was in the range from pH 6.5 to pH 7.5, the activity measured with a given preparation of enzyme was strongly affected by the type of pH buffering system employed. Activity in the presence of Tris buffers was at least 40% lower than with phosphate buffers at the same pH.

The reaction scheme for the reaction catalyzed by the three components of dicamba O-demethylase is presented in FIG. 1. Electrons from NADH are shuttled through a short electron chain consisting of the reductase and ferredoxin to the terminal oxygenase which catalyzes the oxidation of dicamba. The similarities between dicamba O-demethylase and several multicomponent dioxygenases suggest that dicamba O-demethylase may potentially possess cryptic dioxygenase activity. It is clear, however, that this enzyme is not in the class of dioxygenases which split $O_2$ and incorporate one atom of oxygen into the major substrate and the other into a small organic substrate such as α-ketoglutarate (Fukumori and Hausinger (1993) *J. Biol. Chem.* 268:24311–24317). Indeed, combinations of highly purified reductase$_{DIC}$, ferredoxin$_{DIC}$, and oxygenase$_{DIC}$ require only $O_2$, NADH, $Mg^{2+}$, $Fe^{2+}$, and dicamba for activity.

Example 2

Identification And Sequencing Of A Clone Coding For The Oxygenase Of Dicamba O-Demethylase Of *Pseudomonas maltophilia* DI-6

As noted in Example 1, the first 29 amino acids of the N-terminal amino acid sequence of oxygenase$_{DIC}$ had been determined to be (residues in parentheses are best guesses):

[SEQ ID NO:1]
Thr Phe Val Arg Asn Ala Trp Tyr Val Ala Ala Leu Pro

Glu Glu Leu Ser Glu Lys Pro Leu Gly Arg Thr Ile Leu

Asp (Asp or Thr) (Pro).

This sequence permitted the design of degenerate oligonucleotide probes which were synthesized by Operon, Alameda, Calif. In particular, a mixture of 32 probes, each of which was 17 nucleotides in length, and contained all of the possible nucleotide sequences which could encode the amino acid sequence highlighted in bold above, was used. The oligonucleotide probes were 3'-end-labeled with digoxigenin (DIG) according to instructions provided by Boehringer Mannheim, Indianapolis, Ind.

The DIG-labeled probes were first hybridized to *P. maltophilia* DI-6 genomic DNA which had been digested with various combinations of restriction enzymes, resolved on a 1% agarose gel, and blotted to a nylon filter. Based on these results, a size-fractionated genomic library was constructed in the pBluescript II KS+vector and transformed into *Escherichia coli* DH5α competent cells. The genomic library contained 1–2 kb Xho I/Hind III fragments. The DIG-labeled oligonucleotide probes were hybridized to an array of bacterial colonies streaked on nylon filters. Plasmid DNA was isolated from positive colonies and subcloned. Both strands of each subclone were sequenced by the DNA Sequencing Facility at the University of Nebraska-Lincoln. Hybridization and detection of DIG-labeled probes were performed according to protocols provided by Boehringer Mannheim.

A genomic DNA clone coding for the oxygenase$_{DIC}$ was identified. The nucleotide sequence and the deduced amino acid sequence of the entire oxygenase$_{DIC}$ are given in the Sequence Listing below as SEQ ID NO:3 and SEQ ID NO:4, respectively.

A comparison of the amino acid sequence derived from the nucleotide sequence of this clone with that of the protein sequences in the Swiss Protein Database showed homology to other oxygenases. Homology was determined using the FASTA program of the GCG software package. The strongest homology was with the oxygenase component of vanillate demethylase (from *Pseudomonas* sp., ATCC strain 19151) which showed 33.8% identity.

Example 3

Identification And Sequencing Of A Clone Coding For The Ferredoxin Of Dicamba O-Demethylase Of *Pseudomonas* maltophilia DI-6

As noted in Example 1, the first 20 amino acids of the N-terminal amino acid sequence of ferredoxin$_{DIC}$ were determined to be:

[SEQ ID NO:2]
Thr Tyr Val Val Thr Asp Ala Xaa Ile Lys Xaa Lys Tyr

Met Asp Xaa Val Glu Val Xaa.

This sequence permitted the design of degenerate oligonucleotide probes. In particular, a mixture of 16 probes, each of which was 17 nucleotides in length, and contained all the possible nucleotide sequences which could encode the amino acid sequence highlighted in bold above (taking Xaa to be Cys), was used.

DIG-labeled probes were used to screen a genomic library as described in Example 2, except that the genomic library contained 2–3 kb Xho I/Eco RI fragments. The nucleotide sequence of the ferredoxin$_{DIC}$ clone and the deduced amino acid sequence of the entire ferredoxin$_{DIC}$ are given as SEQ ID NO:5 and SEQ ID NO:6, respectively, in the Sequence Listing below.

A comparison of the amino acid sequence derived from the nucleotide sequence of this clone with that of the protein sequences in the Swiss Protein Database was made using the FASTA program of the GCG software package. This comparison showed strong homology to other ferredoxins, including ferredoxins from *Pseudomonas stutzeri*, *Pseudomonas putida*, *Rhodobacter capsulatus*, *Azotobacter vinelandii* and *Rhodospirillum rubrum* (see discussion in Example 1 above).

We claim:

1. An isolated DNA molecule comprising the nucleotide sequence of SEQ ID NO:3.

2. An isolated DNA molecule comprising a DNA sequence encoding a dicamba-degrading oxygenase having the amino acid sequence of SEQ ID NO:4.

3. A DNA construct comprising the nucleotide sequence of SEQ ID NO:3 operatively linked to expression control sequences.

4. The DNA construct of claim 3 which is a vector.

5. A DNA construct comprising a DNA sequence encoding a dicamba-degrading oxygenase having the amino acid sequence of SEQ ID NO:4.

6. A transgenic host cell comprising DNA encoding a dicamba-degrading oxygenase having the amino acid sequence of SEQ ID NO:4, said DNA being operatively linked to expression control sequences.

7. The transgenic host cell of claim 6 wherein the DNA comprises, the nucleotide sequence of SEQ ID NO:3.

8. The transgenic host cell of any one of claims 6 or 7 which is a plant cell.

9. A transgenic plant or part of said transgenic plant comprising one or more cells comprising DNA encoding a dicamba-degrading oxygenase having the amino acid sequence of SEQ ID NO:4.

10. The transgenic plant or plant part of claim 9 wherein the DNA comprises the nucleotide sequence of SEQ ID NO:3.

11. The transgenic plant or plant part of claim 9 wherein the plant is a broadleaf plant which is tolerant to dicamba as a result of the expression of the dicamba-degrading oxygenase and the plant part is a part of a broadleaf plant which is tolerant to dicamba as a result of the expression of the dicamba-degrading oxygenase.

12. A method of controlling weeds in a field containing a transgenic plant according to any one of claims 9, 10 or 11, comprising applying an amount of dicamba to the field effective to control the weeds in the field.

13. A method of selecting transformed plant cells comprising:
   providing a population of plant cells;
   transforming at least some of the plant cells in the population of plant cells with the DNA construct according to any one of claims 3 or 5; and
   selecting the transformed plant cells by culturing the resulting population of plant cells in a culture medium containing dicamba at a concentration selected so that transformed plant cells proliferate and untransformed plant cells do not proliferate.

14. A method of selecting transformed plants comprising:
   providing a population of plants which comprises one or more plants comprising the DNA construct according to any one of claims 3 or 5; and
   selecting transformed plants by applying an amount of dicamba to the population of plants selected so that transformed plants grow, and growth of untransformed plants is inhibited.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 29 amino acids
      (B) TYPE: amino acid
      (C) STRANDEDNESS: single
      (D) TOPOLOGY: linear (ii) MOLECULE TYPE: protein (ix) FEATURE:
      (A) NAME/KEY: Region
      (B) LOCATION: 28
      (D) OTHER INFORMATION: /note= "Best guess for Xaa = Asp or
         Thr"

(ix) FEATURE:
      (A) NAME/KEY: Region
      (B) LOCATION: 29
      (D) OTHER INFORMATION: /note= "Best guess for Xaa = Pro"

(xi) SEQUENCE DESCRIPTION: SEQ ID NO:1:

Thr Phe Val Arg Asn Ala Trp Tyr Val Ala Ala Leu Pro Glu Glu Leu
1               5                  10                  15

Ser Glu Lys Pro Leu Gly Arg Thr Ile Leu Asp Xaa Xaa
            20                  25

(2) INFORMATION FOR SEQ ID NO:2:

(i) SEQUENCE CHARACTERISTICS:
      (A) LENGTH: 20 amino acids
      (B) TYPE: amino acid
      (C) STRANDEDNESS: single
      (D) TOPOLOGY: linear (ii) MOLECULE TYPE: protein (ix) FEATURE:
      (A) NAME/KEY: Region
      (B) LOCATION: 8
      (D) OTHER INFORMATION: /note= "Best guess for Xaa = Cys"

(ix) FEATURE:
      (A) NAME/KEY: Region
      (B) LOCATION: 11
      (D) OTHER INFORMATION: /note= "Best guess for Xaa = Cys"

(ix) FEATURE:
      (A) NAME/KEY: Region
      (B) LOCATION: 16
      (D) OTHER INFORMATION: /note= "Best guess for Xaa = Cys"

(ix) FEATURE:
      (A) NAME/KEY: Region
      (B) LOCATION: 20
      (D) OTHER INFORMATION: /note= "Best guess for Xaa = Cys"

(xi) SEQUENCE DESCRIPTION: SEQ ID NO:2:

Thr Tyr Val Val Thr Asp Ala Xaa Ile Lys Xaa Lys Tyr Met Asp Xaa
1               5                  10                  15

Val Glu Val Xaa
            20

(2) INFORMATION FOR SEQ ID NO:3:

(i) SEQUENCE CHARACTERISTICS:
    (A) LENGTH: 1020 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: CDS
    (B) LOCATION: 1..1020

(xi) SEQUENCE DESCRIPTION: SEQ ID NO:3:

```
ATG ACC TTC GTC CGC AAT GCC TGG TAT GTG GCG GCG CTG CCC GAG GAA        48
Met Thr Phe Val Arg Asn Ala Trp Tyr Val Ala Ala Leu Pro Glu Glu
 1               5                  10                  15

CTG TCC GAA AAG CCG CTC GGC CGG ACG ATT CTC GAC ACA CCG CTC GCG        96
Leu Ser Glu Lys Pro Leu Gly Arg Thr Ile Leu Asp Thr Pro Leu Ala
                20                  25                  30

CTC TAC CGC CAG CCC GAC GGT GTG GTC GCG GCG CTG CTC GAC ATC TGT       144
Leu Tyr Arg Gln Pro Asp Gly Val Val Ala Ala Leu Leu Asp Ile Cys
            35                  40                  45

CCG CAC CGC TTC GCG CCG CTG AGC GAC GGC ATC CTC GTC AAC GGC CAT       192
Pro His Arg Phe Ala Pro Leu Ser Asp Gly Ile Leu Val Asn Gly His
 50                  55                  60

CTC CAA TGC CCC TAT CAC GGG CTG GAA TTC GAT GGC GGC GGG CAG TGC       240
Leu Gln Cys Pro Tyr His Gly Leu Glu Phe Asp Gly Gly Gly Gln Cys
 65                  70                  75                  80

GTC CAT AAC CCG CAC GGC AAT GGC GCC CGC CCG GCT TCG CTC AAC GTC       288
Val His Asn Pro His Gly Asn Gly Ala Arg Pro Ala Ser Leu Asn Val
                85                  90                  95

CGC TCC TTC CCG GTG GTG GAG CGC GAC GCG CTG ATC TGG ATC TGG CCC       336
Arg Ser Phe Pro Val Val Glu Arg Asp Ala Leu Ile Trp Ile Trp Pro
                100                 105                 110

GGC GAT CCG GCG CTG GCC GAT CCT GGG GCG ATC CCC GAC TTC GGC TGC       384
Gly Asp Pro Ala Leu Ala Asp Pro Gly Ala Ile Pro Asp Phe Gly Cys
            115                 120                 125

CGC GTC GAT CCC GCC TAT CGG ACC GTC GGC GGC TAT GGG CAT GTC GAC       432
Arg Val Asp Pro Ala Tyr Arg Thr Val Gly Gly Tyr Gly His Val Asp
 130                 135                 140

TGC AAC TAC AAG CTG CTG GTC GAC AAC CTG ATG GAC CTC GGC CAC GCC       480
Cys Asn Tyr Lys Leu Leu Val Asp Asn Leu Met Asp Leu Gly His Ala
 145                 150                 155                 160

CAA TAT GTC CAT CGC GCC AAC GCC CAG ACC GAC GCC TTC GAC CGG CTG       528
Gln Tyr Val His Arg Ala Asn Ala Gln Thr Asp Ala Phe Asp Arg Leu
                165                 170                 175

GAG CGC GAG GTG ATC GTC GGC GAC GGT GAG ATA CAG GCG CTG ATG AAG       576
Glu Arg Glu Val Ile Val Gly Asp Gly Glu Ile Gln Ala Leu Met Lys
                180                 185                 190

ATT CCC GGC GGC ACG CCG AGC GTG CTG ATG GCC AAG TTC CTG CGC GGC       624
Ile Pro Gly Gly Thr Pro Ser Val Leu Met Ala Lys Phe Leu Arg Gly
            195                 200                 205

GCC AAT ACC CCC GTC GAC GCT TGG AAC GAC ATC CGC TGG AAC AAG GTG       672
Ala Asn Thr Pro Val Asp Ala Trp Asn Asp Ile Arg Trp Asn Lys Val
 210                 215                 220

AGC GCG ATG CTC AAC TTC ATC GCG GTG GCG CCG GAA GGC ACC CCG AAG       720
Ser Ala Met Leu Asn Phe Ile Ala Val Ala Pro Glu Gly Thr Pro Lys
 225                 230                 235                 240

GAG CAG AGC ATC CAC TCG CGC GGT ACC CAT ATC CTG ACC CCC GAG ACG       768
Glu Gln Ser Ile His Ser Arg Gly Thr His Ile Leu Thr Pro Glu Thr
                245                 250                 255

GAG GCG AGC TGC CAT TAT TTC TTC GGC TCC TCG CGC AAT TTC GGC ATC       816
Glu Ala Ser Cys His Tyr Phe Phe Gly Ser Ser Arg Asn Phe Gly Ile
```

-continued

```
Glu Ala Ser Cys His Tyr Phe Phe Gly Ser Ser Arg Asn Phe Gly Ile
            260                 265                 270

GAC GAT CCG GAG ATG GAC GGC GTG CTG CGC AGC TGG CAG GCT CAG GCG         864
Asp Asp Pro Glu Met Asp Gly Val Leu Arg Ser Trp Gln Ala Gln Ala
        275                 280                 285

CTG GTC AAG GAG GAC AAG GTC GTC GTC GAG GCG ATC GAG CGC CGC CGC         912
Leu Val Lys Glu Asp Lys Val Val Val Glu Ala Ile Glu Arg Arg Arg
290                 295                 300

GCC TAT GTC GAG GCG AAT GGC ATC CGC CCG GCG ATG CTG TCG TGC GAC         960
Ala Tyr Val Glu Ala Asn Gly Ile Arg Pro Ala Met Leu Ser Cys Asp
305                 310                 315                 320

GAA GCC GCA GTC CGT GTC AGC CGC GAG ATC GAG AAG CTT GAG CAG CTC        1008
Glu Ala Ala Val Arg Val Ser Arg Glu Ile Glu Lys Leu Glu Gln Leu
                325                 330                 335

GAA GCC GCC TGA                                                        1020
Glu Ala Ala  *
        340
```

(2) INFORMATION FOR SEQ ID NO:4:

(i) SEQUENCE CHARACTERISTICS:
      (A) LENGTH: 339 amino acids
      (B) TYPE: amino acid
      (D) TOPOLOGY: linear (ii) MOLECULE TYPE: protein (xi) SEQUENCE DESCRIPTION: SEQ ID NO:4:

```
Met Thr Phe Val Arg Asn Ala Trp Tyr Val Ala Ala Leu Pro Glu Glu
1               5                   10                  15

Leu Ser Glu Lys Pro Leu Gly Arg Thr Ile Leu Asp Thr Pro Leu Ala
            20                  25                  30

Leu Tyr Arg Gln Pro Asp Gly Val Val Ala Ala Leu Leu Asp Ile Cys
        35                  40                  45

Pro His Arg Phe Ala Pro Leu Ser Asp Gly Ile Leu Val Asn Gly His
    50                  55                  60

Leu Gln Cys Pro Tyr His Gly Leu Glu Phe Asp Gly Gly Gly Gln Cys
65                  70                  75                  80

Val His Asn Pro His Gly Asn Gly Ala Arg Pro Ala Ser Leu Asn Val
                85                  90                  95

Arg Ser Phe Pro Val Val Glu Arg Asp Ala Leu Ile Trp Ile Trp Pro
            100                 105                 110

Gly Asp Pro Ala Leu Ala Asp Pro Gly Ala Ile Pro Asp Phe Gly Cys
        115                 120                 125

Arg Val Asp Pro Ala Tyr Arg Thr Val Gly Tyr Gly His Val Asp
    130                 135                 140

Cys Asn Tyr Lys Leu Leu Val Asp Asn Leu Met Asp Leu Gly His Ala
145                 150                 155                 160

Gln Tyr Val His Arg Ala Asn Ala Gln Thr Asp Ala Phe Asp Arg Leu
                165                 170                 175

Glu Arg Glu Val Ile Val Gly Asp Gly Glu Ile Gln Ala Leu Met Lys
            180                 185                 190

Ile Pro Gly Gly Thr Pro Ser Val Leu Met Ala Lys Phe Leu Arg Gly
        195                 200                 205

Ala Asn Thr Pro Val Asp Ala Trp Asn Asp Ile Arg Trp Asn Lys Val
    210                 215                 220

Ser Ala Met Leu Asn Phe Ile Ala Val Ala Pro Glu Gly Thr Pro Lys
225                 230                 235                 240
```

```
Glu Gln Ser Ile His Ser Arg Gly Thr His Ile Leu Thr Pro Glu Thr
            245                 250                 255

Glu Ala Ser Cys His Tyr Phe Phe Gly Ser Ser Arg Asn Phe Gly Ile
            260                 265                 270

Asp Asp Pro Glu Met Asp Gly Val Leu Arg Ser Trp Gln Ala Gln Ala
            275                 280                 285

Leu Val Lys Glu Asp Lys Val Val Glu Ala Ile Glu Arg Arg
            290                 295                 300

Ala Tyr Val Glu Ala Asn Gly Ile Arg Pro Ala Met Leu Ser Cys Asp
305                 310                 315                 320

Glu Ala Ala Val Arg Val Ser Arg Glu Ile Glu Lys Leu Glu Gln Leu
            325                 330                 335

Glu Ala Ala
        340

(2) INFORMATION FOR SEQ ID NO:5:

(i) SEQUENCE CHARACTERISTICS:
        (A) LENGTH: 339 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..339

(xi) SEQUENCE DESCRIPTION: SEQ ID NO:5:

ATG ACC TAT GTC GTC ACC GAC GCC TGC ATC AAG TGC AAG TAC ATG GAC      48
Met Thr Tyr Val Val Thr Asp Ala Cys Ile Lys Cys Lys Tyr Met Asp
 1               5                  10                  15

TGC GTG GAA GTC TGC CCT GTG GAC TGC TTC TAC GAA GGC GAG AAC ATG      96
Cys Val Glu Val Cys Pro Val Asp Cys Phe Tyr Glu Gly Glu Asn Met
                20                  25                  30

CTC GTC ATC AAT CCC AGT GAA TGC ATC GAC TGC GGC GTC TGC GAA CCG     144
Leu Val Ile Asn Pro Ser Glu Cys Ile Asp Cys Gly Val Cys Glu Pro
            35                  40                  45

GAA TGC CCA GCC GAA GCC ATC CTT CCC GAC ACC GAA AGC GGT CTC GAG     192
Glu Cys Pro Ala Glu Ala Ile Leu Pro Asp Thr Glu Ser Gly Leu Glu
 50                  55                  60

CAG TGG ATG GAA CTG AAC ACG AAG TAC TCG GCC GAG TGG CCG AAT CTC     240
Gln Trp Met Glu Leu Asn Thr Lys Tyr Ser Ala Glu Trp Pro Asn Leu
 65                  70                  75                  80

ACG TCC AAG AAA GAT TCG CCG GAA GAT GCC GAC GAG TAC AAG GGC GTG     288
Thr Ser Lys Lys Asp Ser Pro Glu Asp Ala Asp Glu Tyr Lys Gly Val
                85                  90                  95

GAA GGC AAG TTC GAG AAG TTC TTC TCG CCC GAG CCC GGC GAG GGC GAC     336
Glu Gly Lys Phe Glu Lys Phe Phe Ser Pro Glu Pro Gly Glu Gly Asp
             100                 105                 110

TGA                                                                  339
 *

(2) INFORMATION FOR SEQ ID NO:6:

(i) SEQUENCE CHARACTERISTICS:
        (A) LENGTH:  112 amino acids
        (B) TYPE: amino acid
        (D) TOPOLOGY: linear (ii) MOLECULE TYPE: protein
```

```
   (xi) SEQUENCE DESCRIPTION: SEQ ID NO:6:

Met Thr Tyr Val Val Thr Asp Ala Cys Ile Lys Cys Lys Tyr Met Asp
 1               5                  10                 15

Cys Val Glu Val Cys Pro Val Asp Cys Phe Tyr Glu Gly Glu Asn Met
            20                  25                 30

Leu Val Ile Asn Pro Ser Glu Cys Ile Asp Cys Gly Val Cys Glu Pro
            35                  40                 45

Glu Cys Pro Ala Glu Ala Ile Leu Pro Asp Thr Glu Ser Gly Leu Glu
        50                  55                 60

Gln Trp Met Glu Leu Asn Thr Lys Tyr Ser Ala Glu Trp Pro Asn Leu
 65                  70                 75                  80

Thr Ser Lys Lys Asp Ser Pro Glu Asp Ala Asp Glu Tyr Lys Gly Val
                85                  90                 95

Glu Gly Lys Phe Glu Lys Phe Phe Ser Pro Glu Pro Gly Glu Gly Asp
               100                 105                110
```